US010932811B2

(12) United States Patent
Guggenheimer et al.

(10) Patent No.: US 10,932,811 B2
(45) Date of Patent: Mar. 2, 2021

(54) TISSUE-REMOVING CATHETER WITH ROTATABLE CUTTER

(71) Applicant: Covidien LP, Mansfield, MA (US)

(72) Inventors: Ethan A. Guggenheimer, Minnetonka, MN (US); Lucas Schneider, Champlin, MN (US); Thomas McPeak, Shakopee, MN (US); Benjamin Fruland, Blaine, MN (US)

( * ) Notice: Subject to any disclaimer, the term of this patent is extended or adjusted under 35 U.S.C. 154(b) by 386 days.

(21) Appl. No.: 15/816,744

(22) Filed: Nov. 17, 2017

(65) Prior Publication Data

US 2018/0070980 A1    Mar. 15, 2018

Related U.S. Application Data

(63) Continuation of application No. 13/671,695, filed on Nov. 8, 2012, now Pat. No. 9,943,329.

(51) Int. Cl.
*A61B 17/3207* (2006.01)
*A61B 17/32* (2006.01)

(52) U.S. Cl.
CPC ........... *A61B 17/320758* (2013.01); *A61B 17/320783* (2013.01); *A61B 2017/320004* (2013.01);
(Continued)

(58) Field of Classification Search
CPC ........ A61B 17/320758; A61B 2017/32; A61B 17/320783; A61B 2017/32077; A61B 2017/32079
See application file for complete search history.

(56) References Cited

U.S. PATENT DOCUMENTS

| 1,481,078 A | 1/1924 | Albertson |
| 2,178,790 A | 11/1939 | Henry |

(Continued)

FOREIGN PATENT DOCUMENTS

| CA | 2000621 A1 | 4/1990 |
| DE | 3732236 C1 | 12/1988 |

(Continued)

OTHER PUBLICATIONS

European Extended Search Report for Application No. 18200126.3, dated Nov. 12, 2018, 8 pages.

(Continued)

*Primary Examiner* — Richard G Louis
(74) *Attorney, Agent, or Firm* — Stinson LLP

(57) ABSTRACT

A tissue-removing catheter includes a cutting element. A radially innermost portion of the leading radial wall of a raised element of the cutting element may be spaced a radial distance from the longitudinal axis that is less than 66% of the radius of the annular cutting edge. The cutting element may be extendable through the window during operation such that as the cutting element is being rotated about its longitudinal axis, less than an entire radial portion of the leading radial wall passes through the window. A plurality of abrading members may be formed on at least the central portion of the inner surface of the cutting element to abrade hardened tissue as the cutting element is rotating about its longitudinal axis. A radially outermost portion of the leading radial edge of the raised element may be spaced apart radially from an inner surface of the cutting element.

9 Claims, 25 Drawing Sheets

(52) U.S. Cl.
CPC ............ *A61B 2017/320775* (2013.01); *A61B 2017/320791* (2013.01)

(56) References Cited

U.S. PATENT DOCUMENTS

| | | |
|---|---|---|
| 2,701,559 A | 2/1955 | Cooper |
| 2,850,007 A | 9/1958 | Lingley |
| 3,064,651 A | 11/1962 | Henderson |
| 3,082,805 A | 3/1963 | Royce |
| 3,320,957 A | 5/1967 | Sokolik |
| 3,614,953 A | 10/1971 | Moss |
| 3,683,891 A | 8/1972 | Eskridge et al. |
| 3,705,577 A | 12/1972 | Sierra |
| 3,732,858 A | 5/1973 | Banko |
| 3,749,085 A | 7/1973 | Wilson et al. |
| 3,800,783 A | 4/1974 | Jamshidi |
| 3,815,604 A | 6/1974 | O'Malley et al. |
| 3,831,585 A | 8/1974 | Brondy et al. |
| 3,837,345 A | 9/1974 | Matar |
| 3,845,375 A | 10/1974 | Stiebel |
| 3,937,222 A | 2/1976 | Banko |
| 3,945,375 A | 3/1976 | Banko |
| 3,976,077 A | 8/1976 | Kerfoot, Jr. |
| 3,995,619 A | 12/1976 | Glatzer |
| 4,007,732 A | 2/1977 | Kvavle et al. |
| 4,020,847 A | 5/1977 | Clark, III |
| 4,030,503 A | 6/1977 | Clark, III |
| 4,034,744 A | 7/1977 | Goldberg |
| 4,038,985 A | 8/1977 | Chiulli |
| 4,112,708 A | 9/1978 | Fukuda |
| 4,177,797 A | 12/1979 | Baylis et al. |
| 4,210,146 A | 7/1980 | Banko |
| 4,273,128 A | 6/1981 | Lary |
| 4,306,562 A | 12/1981 | Osborne |
| 4,306,570 A | 12/1981 | Matthews |
| 4,349,032 A | 9/1982 | Koyata |
| 4,368,730 A | 1/1983 | Sharrock |
| 4,424,045 A | 1/1984 | Kulischenko et al. |
| 4,436,091 A | 3/1984 | Blanko |
| 4,445,509 A | 5/1984 | Auth |
| 4,490,139 A | 12/1984 | Huizenga et al. |
| 4,494,057 A | 1/1985 | Hotta |
| 4,512,344 A | 4/1985 | Barber |
| 4,589,412 A | 5/1986 | Kensey |
| 4,603,694 A | 8/1986 | Wheeler |
| 4,620,547 A | 11/1986 | Boebel |
| 4,631,052 A | 12/1986 | Kensey |
| 4,646,719 A | 3/1987 | Neuman et al. |
| 4,646,736 A | 3/1987 | Auth |
| 4,646,738 A | 3/1987 | Trott |
| 4,649,919 A | 3/1987 | Thimsen et al. |
| 4,653,496 A | 3/1987 | Bundy et al. |
| 4,664,112 A | 5/1987 | Kensey et al. |
| 4,669,469 A | 6/1987 | Gifford, III et al. |
| 4,686,982 A | 8/1987 | Nash |
| 4,692,141 A | 9/1987 | Mahurkar |
| 4,696,298 A | 9/1987 | Higgins et al. |
| 4,696,667 A | 9/1987 | Masch |
| 4,705,038 A | 11/1987 | Sjostrom et al. |
| 4,706,671 A | 11/1987 | Weinrib |
| 4,728,319 A | 3/1988 | Masch |
| 4,729,763 A | 3/1988 | Henrie |
| 4,730,616 A | 3/1988 | Frisbie et al. |
| 4,732,154 A | 3/1988 | Shiber |
| 4,733,662 A | 3/1988 | DeSatnick et al. |
| 4,747,406 A | 5/1988 | Nash |
| 4,747,821 A | 5/1988 | Kensey et al. |
| 4,749,376 A | 6/1988 | Kensey et al. |
| 4,754,755 A | 7/1988 | Husted |
| 4,757,819 A | 7/1988 | Yokoi et al. |
| 4,765,332 A | 8/1988 | Fischell et al. |
| 4,771,774 A | 9/1988 | Simpson et al. |
| 4,781,186 A | 11/1988 | Simpson et al. |
| 4,784,636 A | 11/1988 | Rydell |
| 4,790,812 A | 12/1988 | Hawkins, Jr. et al. |
| 4,794,931 A | 1/1989 | Yock |
| 4,817,613 A | 4/1989 | Jaraczewski et al. |
| 4,819,634 A | 4/1989 | Shiber |
| 4,819,635 A | 4/1989 | Shapiro |
| 4,838,268 A | 6/1989 | Keith et al. |
| 4,842,579 A | 6/1989 | Shiber |
| 4,844,064 A | 7/1989 | Thimsen et al. |
| 4,846,192 A | 7/1989 | MacDonald |
| 4,848,343 A | 7/1989 | Vvallsten et al. |
| 4,850,957 A | 7/1989 | Summers |
| 4,857,046 A | 8/1989 | Stevens et al. |
| 4,867,157 A | 9/1989 | McGurk-Burleson et al. |
| 4,870,953 A | 10/1989 | DonMicheal et al. |
| 4,883,458 A | 11/1989 | Shiber |
| 4,886,061 A | 12/1989 | Fischell et al. |
| 4,886,490 A | 12/1989 | Shiber |
| 4,887,613 A | 12/1989 | Farr et al. |
| 4,894,051 A | 1/1990 | Shiber |
| 4,899,757 A | 2/1990 | Pope, Jr. et al. |
| 4,919,133 A | 4/1990 | Chiang |
| 4,923,462 A | 5/1990 | Stevens |
| 4,926,858 A | 5/1990 | Gifford, III et al. |
| 4,928,693 A | 5/1990 | Goodin et al. |
| 4,936,987 A | 6/1990 | Persinski et al. |
| RE33,258 E | 7/1990 | Onik et al. |
| 4,950,238 A | 8/1990 | Sullivan |
| 4,954,338 A | 9/1990 | Mattox |
| 4,957,482 A | 9/1990 | Shiber |
| 4,966,604 A | 10/1990 | Reiss |
| 4,973,409 A | 11/1990 | Cook |
| 4,979,939 A | 12/1990 | Shiber |
| 4,979,951 A | 12/1990 | Simpson |
| 4,986,807 A | 1/1991 | Farr |
| 4,990,134 A | 2/1991 | Auth |
| 4,994,067 A | 2/1991 | Summers |
| 4,997,435 A | 3/1991 | Demeter |
| 5,000,185 A | 3/1991 | Yock |
| 5,002,553 A | 3/1991 | Shiber |
| 5,003,918 A | 4/1991 | Olson et al. |
| 5,007,896 A | 4/1991 | Shiber |
| 5,007,917 A | 4/1991 | Evans |
| 5,009,659 A | 4/1991 | Hamlin et al. |
| 5,011,490 A | 4/1991 | Fischell et al. |
| 5,019,088 A | 5/1991 | Farr |
| 5,024,234 A | 6/1991 | Leary et al. |
| 5,024,651 A | 6/1991 | Shiber |
| 5,026,384 A | 6/1991 | Farr et al. |
| 5,029,588 A | 7/1991 | Yock et al. |
| 5,030,201 A | 7/1991 | Palestrant |
| 5,047,040 A | 9/1991 | Simpson et al. |
| 5,049,124 A | 9/1991 | Bales, Jr. |
| 5,053,044 A | 10/1991 | Mueller et al. |
| 5,054,492 A | 10/1991 | Scribner et al. |
| 5,061,273 A | 10/1991 | Yock |
| 5,064,435 A | 11/1991 | Porter |
| 5,071,425 A | 12/1991 | Gifford, III et al. |
| 5,074,841 A | 12/1991 | Ademovic et al. |
| 5,077,506 A | 12/1991 | Krause |
| 5,078,722 A | 1/1992 | Stevens |
| 5,078,723 A | 1/1992 | Dance et al. |
| 5,084,010 A | 1/1992 | Plaia et al. |
| 5,085,662 A | 2/1992 | Willard |
| 5,087,265 A | 2/1992 | Summers |
| 5,092,839 A | 3/1992 | Kipperman |
| 5,092,873 A | 3/1992 | Simpson et al. |
| 5,095,911 A | 3/1992 | Pomeranz |
| 5,100,423 A | 3/1992 | Fearnot |
| 5,100,424 A | 3/1992 | Jang et al. |
| 5,100,426 A | 3/1992 | Nixon |
| 5,101,806 A | 4/1992 | Hunt et al. |
| 5,108,500 A | 4/1992 | Mattox |
| 5,110,822 A | 5/1992 | Sherba et al. |
| 5,112,345 A | 5/1992 | Farr |
| 5,114,399 A | 5/1992 | Kovalcheck |
| 5,115,814 A | 5/1992 | Griffith et al. |
| 5,116,352 A | 5/1992 | Schnepp-Pesch et al. |
| 5,120,323 A | 6/1992 | Shockey et al. |
| 5,127,902 A | 7/1992 | Fischell |
| 5,127,917 A | 7/1992 | Niederhauser et al. |

(56) References Cited

U.S. PATENT DOCUMENTS

| | | |
|---|---|---|
| 5,135,531 A | 8/1992 | Shiber |
| 5,139,506 A | 8/1992 | Bush |
| 5,154,705 A | 10/1992 | Fleischhacker et al. |
| 5,154,724 A | 10/1992 | Andrews |
| 5,165,421 A | 11/1992 | Fleischhacker et al. |
| 5,176,693 A | 1/1993 | Pannek, Jr. |
| 5,178,625 A | 1/1993 | Groshong |
| 5,181,920 A | 1/1993 | Mueller et al. |
| 5,183,432 A | 2/1993 | Noguchi |
| 5,190,528 A | 3/1993 | Fonger et al. |
| 5,192,291 A | 3/1993 | Pannek, Jr. |
| 5,195,956 A | 3/1993 | Stockmeier |
| 5,211,651 A | 5/1993 | Reger et al. |
| 5,217,474 A | 6/1993 | Zacca et al. |
| 5,222,966 A | 6/1993 | Perkins et al. |
| 5,224,488 A | 7/1993 | Neuffer |
| 5,224,945 A | 7/1993 | Pannek, Jr. |
| 5,224,949 A | 7/1993 | Gomringer et al. |
| 5,226,909 A | 7/1993 | Evans et al. |
| 5,226,910 A | 7/1993 | Kajiyama et al. |
| 5,234,451 A | 8/1993 | Osypka |
| 5,242,460 A | 9/1993 | Klein et al. |
| 5,242,461 A | 9/1993 | Kortenbach et al. |
| 5,250,059 A | 10/1993 | Andreas et al. |
| 5,250,065 A | 10/1993 | Clement et al. |
| 5,261,877 A | 11/1993 | Fine et al. |
| 5,263,928 A | 11/1993 | Trauthen et al. |
| 5,263,959 A | 11/1993 | Fischell |
| 5,267,955 A | 12/1993 | Hanson |
| 5,267,982 A | 12/1993 | Sylvanowicz |
| 5,269,793 A | 12/1993 | Simpson |
| 5,273,526 A | 12/1993 | Dance et al. |
| 5,282,484 A | 2/1994 | Reger |
| 5,284,486 A | 2/1994 | Kotula et al. |
| 5,285,795 A | 2/1994 | Ryan et al. |
| 5,290,303 A | 3/1994 | Pingleton et al. |
| 5,295,493 A | 3/1994 | Radisch, Jr. |
| 5,306,294 A | 4/1994 | Winston et al. |
| 5,308,354 A | 5/1994 | Zacca et al. |
| 5,312,427 A | 5/1994 | Shturman |
| 5,314,438 A | 5/1994 | Shturman |
| 5,318,032 A | 6/1994 | Lonsbury et al. |
| 5,318,528 A | 6/1994 | Heaven et al. |
| 5,318,576 A | 6/1994 | Plassche, Jr. et al. |
| 5,321,501 A | 6/1994 | Swanson et al. |
| 5,322,508 A | 6/1994 | Viera |
| 5,336,167 A | 8/1994 | Sullivan et al. |
| 5,350,390 A | 9/1994 | Sher |
| 5,356,418 A | 10/1994 | Shturman |
| 5,358,472 A | 10/1994 | Vance et al. |
| 5,358,485 A | 10/1994 | Vance et al. |
| 5,360,432 A | 11/1994 | Shturman |
| 5,366,463 A | 11/1994 | Ryan |
| 5,368,035 A | 11/1994 | Hamm et al. |
| 5,370,609 A | 12/1994 | Drasler et al. |
| 5,370,651 A | 12/1994 | Summers |
| 5,372,601 A | 12/1994 | Lary |
| 5,372,602 A | 12/1994 | Burke |
| 5,373,849 A | 12/1994 | Maroney et al. |
| 5,377,682 A | 1/1995 | Ueno et al. |
| 5,378,234 A | 1/1995 | Hammerslag et al. |
| 5,383,460 A | 1/1995 | Jang et al. |
| 5,395,311 A | 3/1995 | Andrews |
| 5,395,313 A | 3/1995 | Naves et al. |
| 5,395,335 A | 3/1995 | Jang |
| 5,397,345 A | 3/1995 | Lazarus |
| 5,402,790 A | 4/1995 | Jang et al. |
| 5,409,454 A | 4/1995 | Fischell et al. |
| 5,413,107 A | 5/1995 | Oakley et al. |
| 5,419,774 A | 5/1995 | Willard et al. |
| 5,421,338 A | 6/1995 | Crowley et al. |
| 5,423,799 A | 6/1995 | Shiu |
| 5,423,846 A | 6/1995 | Fischell |
| 5,427,107 A | 6/1995 | Milo et al. |
| 5,429,136 A | 7/1995 | Milo et al. |
| 5,431,673 A | 7/1995 | Summers et al. |
| 5,441,510 A | 8/1995 | Simpson et al. |
| 5,443,446 A | 8/1995 | Shturman |
| 5,443,497 A | 8/1995 | Venbrux |
| 5,444,078 A | 8/1995 | Yu et al. |
| 5,445,155 A | 8/1995 | Sieben |
| 5,449,369 A | 9/1995 | Imran |
| 5,454,809 A | 10/1995 | Janssen |
| 5,456,667 A | 10/1995 | Ham et al. |
| 5,456,689 A | 10/1995 | Kresch et al. |
| 5,458,585 A | 10/1995 | Salmon et al. |
| 5,459,570 A | 10/1995 | Swanson et al. |
| 5,464,016 A | 11/1995 | Nicholas et al. |
| 5,466,382 A | 11/1995 | Downey et al. |
| 5,485,840 A | 1/1996 | Bauman |
| 5,487,729 A | 1/1996 | Avellanet et al. |
| 5,489,295 A | 2/1996 | Piplani et al. |
| 5,491,524 A | 2/1996 | Hellmuth et al. |
| 5,496,267 A | 3/1996 | Drasler et al. |
| 5,501,694 A | 3/1996 | Ressemann et al. |
| 5,503,155 A | 4/1996 | Salmon et al. |
| 5,505,210 A | 4/1996 | Clement |
| 5,507,760 A | 4/1996 | Wynne et al. |
| 5,507,761 A | 4/1996 | Duer |
| 5,507,769 A | 4/1996 | Marin et al. |
| 5,507,795 A | 4/1996 | Chiang et al. |
| 5,512,044 A | 4/1996 | Duer |
| 5,514,115 A | 5/1996 | Frantzen et al. |
| 5,520,189 A | 5/1996 | Malinowski et al. |
| 5,522,825 A | 6/1996 | Kropf et al. |
| 5,522,880 A | 6/1996 | Barone et al. |
| 5,527,292 A | 6/1996 | Adams et al. |
| 5,527,298 A | 6/1996 | Vance et al. |
| 5,527,325 A | 6/1996 | Conley et al. |
| 5,531,685 A | 7/1996 | Hemmer et al. |
| 5,531,690 A | 7/1996 | Solar |
| 5,531,700 A | 7/1996 | Moore et al. |
| 5,540,707 A | 7/1996 | Ressemann et al. |
| 5,549,601 A | 8/1996 | McIntyre et al. |
| 5,554,163 A | 9/1996 | Shturman |
| 5,556,408 A | 9/1996 | Farhat |
| 5,558,093 A | 9/1996 | Pomeranz |
| 5,562,726 A | 10/1996 | Chuter |
| 5,562,728 A | 10/1996 | Lazarus et al. |
| 5,569,275 A | 10/1996 | Kotula et al. |
| 5,569,279 A | 10/1996 | Rainin |
| 5,571,122 A | 11/1996 | Kelly et al. |
| 5,571,130 A | 11/1996 | Simpson et al. |
| 5,575,817 A | 11/1996 | Martin |
| 5,584,842 A | 12/1996 | Fogarty et al. |
| 5,584,843 A | 12/1996 | Wulfman et al. |
| 5,609,605 A | 3/1997 | Marshall et al. |
| 5,618,293 A | 4/1997 | Sample et al. |
| 5,620,415 A | 4/1997 | Lucey et al. |
| 5,620,447 A | 4/1997 | Smith et al. |
| 5,624,457 A | 4/1997 | Farley et al. |
| 5,626,562 A | 5/1997 | Castro |
| 5,628,761 A | 5/1997 | Rizik |
| 5,632,754 A | 5/1997 | Farley et al. |
| 5,632,755 A | 5/1997 | Nordgren et al. |
| 5,643,296 A | 7/1997 | Hundertmark et al. |
| 5,649,941 A | 7/1997 | Lary |
| 5,662,671 A | 9/1997 | Barbut et al. |
| 5,674,232 A | 10/1997 | Halliburton |
| 5,676,697 A | 10/1997 | McDonald |
| 5,681,336 A | 10/1997 | Clement et al. |
| 5,683,449 A | 11/1997 | Marcade |
| 5,683,453 A | 11/1997 | Palmaz |
| 5,688,234 A | 11/1997 | Frisbie |
| 5,695,506 A | 12/1997 | Pike et al. |
| 5,695,507 A | 12/1997 | Auth et al. |
| 5,697,944 A | 12/1997 | Lary |
| 5,700,240 A | 12/1997 | Barwick, Jr. et al. |
| 5,700,687 A | 12/1997 | Finn |
| 5,707,350 A | 1/1998 | Krause et al. |
| 5,707,376 A | 1/1998 | Kavteladze et al. |
| 5,707,383 A | 1/1998 | Bays et al. |
| 5,709,698 A | 1/1998 | Adams et al. |
| 5,713,913 A | 2/1998 | Lary et al. |

(56) References Cited

U.S. PATENT DOCUMENTS

| | | |
|---|---|---|
| 5,716,410 A | 2/1998 | Wang et al. |
| 5,720,735 A | 2/1998 | Dorros |
| 5,724,977 A | 3/1998 | Yock et al. |
| 5,728,123 A | 3/1998 | Lemelson et al. |
| 5,733,296 A | 3/1998 | Rogers et al. |
| 5,735,816 A | 4/1998 | Lieber et al. |
| 5,741,270 A | 4/1998 | Hansen et al. |
| 5,766,192 A | 6/1998 | Zacca |
| 5,772,674 A | 6/1998 | Nakhjavan |
| 5,775,327 A | 7/1998 | Randolph et al. |
| 5,776,153 A | 7/1998 | Rees |
| 5,779,643 A | 7/1998 | Lum et al. |
| 5,779,673 A | 7/1998 | Roth et al. |
| 5,779,721 A | 7/1998 | Nash |
| 5,779,722 A | 7/1998 | Shturman et al. |
| 5,792,157 A | 8/1998 | Mische et al. |
| 5,797,949 A | 8/1998 | Parodi |
| 5,807,329 A | 9/1998 | Gelman |
| 5,810,867 A | 9/1998 | Zarbatany et al. |
| 5,816,923 A | 10/1998 | Milo et al. |
| 5,820,592 A | 10/1998 | Hammerslag |
| 5,823,971 A | 10/1998 | Robinson et al. |
| 5,824,055 A | 10/1998 | Spiridigliozzi et al. |
| 5,827,201 A | 10/1998 | Samson et al. |
| 5,827,229 A | 10/1998 | Auth et al. |
| 5,827,304 A | 10/1998 | Hart |
| 5,827,322 A | 10/1998 | Williams |
| 5,830,222 A | 11/1998 | Makower |
| 5,830,224 A | 11/1998 | Cohn et al. |
| 5,836,957 A | 11/1998 | Schulz et al. |
| 5,843,022 A | 12/1998 | Willard et al. |
| 5,843,103 A | 12/1998 | Wulfman |
| 5,843,161 A | 12/1998 | Solovay |
| 5,855,563 A | 1/1999 | Kaplan et al. |
| 5,865,748 A | 2/1999 | Co et al. |
| 5,868,685 A | 2/1999 | Powell et al. |
| 5,868,767 A | 2/1999 | Farley et al. |
| 5,871,536 A | 2/1999 | Lazarus |
| 5,873,882 A | 2/1999 | Straub et al. |
| 5,876,414 A | 3/1999 | Straub |
| 5,879,361 A | 3/1999 | Nash |
| 5,879,397 A | 3/1999 | Kalberer et al. |
| 5,883,458 A | 3/1999 | Sumita et al. |
| 5,888,201 A | 3/1999 | Stinson et al. |
| 5,895,399 A | 4/1999 | Barbut et al. |
| 5,910,150 A | 6/1999 | Saadat |
| 5,911,734 A | 6/1999 | Tsugita et al. |
| 5,916,210 A | 6/1999 | Winston |
| 5,922,003 A | 7/1999 | Anctil et al. |
| 5,935,108 A | 8/1999 | Katoh et al. |
| 5,938,645 A | 8/1999 | Gordon |
| 5,938,671 A | 8/1999 | Katoh et al. |
| 5,941,869 A | 8/1999 | Patterson et al. |
| 5,947,985 A | 9/1999 | Imran |
| 5,951,480 A | 9/1999 | White et al. |
| 5,951,482 A | 9/1999 | Winston et al. |
| 5,954,745 A | 9/1999 | Gertler et al. |
| 5,968,064 A | 10/1999 | Selmon et al. |
| 5,972,019 A | 10/1999 | Engelson et al. |
| 5,985,397 A | 11/1999 | Witt et al. |
| 5,989,281 A | 11/1999 | Barbut et al. |
| 6,001,112 A | 12/1999 | Taylor |
| 6,010,449 A | 1/2000 | Selmon et al. |
| 6,010,522 A | 1/2000 | Barbut et al. |
| 6,013,072 A | 1/2000 | Winston et al. |
| 6,019,778 A | 2/2000 | Wilson et al. |
| 6,022,362 A | 2/2000 | Lee et al. |
| 6,027,450 A | 2/2000 | Brown et al. |
| 6,027,460 A | 2/2000 | Shturman |
| 6,027,514 A | 2/2000 | Stine et al. |
| 6,032,673 A | 3/2000 | Savage et al. |
| 6,036,646 A | 3/2000 | Barthe et al. |
| 6,036,656 A | 3/2000 | Slater |
| 6,036,707 A | 3/2000 | Spaulding |
| 6,039,693 A | 3/2000 | Seward et al. |
| 6,048,349 A | 4/2000 | Winston et al. |
| 6,050,949 A | 4/2000 | White et al. |
| 6,066,153 A | 5/2000 | Lev |
| 6,068,603 A | 5/2000 | Suzuki |
| 6,081,738 A | 6/2000 | Hinohara et al. |
| RE36,764 E | 7/2000 | Zacca et al. |
| 6,095,990 A | 8/2000 | Parodi |
| 6,106,515 A | 8/2000 | Winston et al. |
| 6,110,121 A | 8/2000 | Lenker |
| 6,120,516 A | 9/2000 | Selmon et al. |
| 6,126,649 A | 10/2000 | VanTassel et al. |
| 6,129,734 A | 10/2000 | Shturman et al. |
| 6,134,003 A | 10/2000 | Tearney et al. |
| 6,152,909 A | 11/2000 | Bagaoisan et al. |
| 6,152,938 A | 11/2000 | Curry |
| 6,156,046 A | 12/2000 | Passafaro et al. |
| 6,157,852 A | 12/2000 | Selmon et al. |
| 6,159,195 A | 12/2000 | Ha et al. |
| 6,179,859 B1 | 1/2001 | Bates et al. |
| 6,183,432 B1 | 2/2001 | Milo |
| 6,187,025 B1 | 2/2001 | Machek |
| 6,190,353 B1 | 2/2001 | Makower et al. |
| 6,191,862 B1 | 2/2001 | Swanson et al. |
| 6,193,676 B1 | 2/2001 | Winston et al. |
| 6,196,963 B1 | 3/2001 | Williams |
| 6,206,898 B1 | 3/2001 | Honeycutt et al. |
| 6,217,527 B1 | 4/2001 | Selmon et al. |
| 6,217,549 B1 | 4/2001 | Selmon et al. |
| 6,217,595 B1 | 4/2001 | Shturman et al. |
| 6,221,006 B1 | 4/2001 | Dubrul et al. |
| 6,221,076 B1 | 4/2001 | Albrektsson et al. |
| 6,221,332 B1 | 4/2001 | Thumm et al. |
| 6,228,049 B1 | 5/2001 | Schroeder et al. |
| 6,228,076 B1 | 5/2001 | Winston et al. |
| 6,231,546 B1 | 5/2001 | Milo et al. |
| 6,231,549 B1 | 5/2001 | Noecker et al. |
| 6,238,405 B1 | 5/2001 | Findlay, III et al. |
| 6,241,667 B1 | 6/2001 | Vetter et al. |
| 6,241,744 B1 | 6/2001 | Imran et al. |
| 6,245,012 B1 | 6/2001 | Kleshinski |
| 6,263,236 B1 | 7/2001 | Kasinkas et al. |
| 6,264,611 B1 | 7/2001 | Ishikawa et al. |
| 6,277,138 B1 | 8/2001 | Levinson et al. |
| 6,283,951 B1 | 9/2001 | Flaherty et al. |
| 6,283,983 B1 | 9/2001 | Makower et al. |
| 6,299,622 B1 | 10/2001 | Snow et al. |
| 6,299,623 B1 | 10/2001 | Wulfman |
| 6,302,875 B1 | 10/2001 | Makower et al. |
| 6,305,834 B1 | 10/2001 | Schubert et al. |
| 6,312,444 B1 | 11/2001 | Barbut |
| 6,319,275 B1 | 11/2001 | Lashinski et al. |
| 6,330,884 B1 | 12/2001 | Kim |
| 6,361,545 B1 | 3/2002 | Macoviak et al. |
| 6,375,615 B1 | 4/2002 | Flaherty et al. |
| 6,383,195 B1 | 5/2002 | Richard |
| 6,383,205 B1 | 5/2002 | Samson et al. |
| 6,394,976 B1 | 5/2002 | Winston et al. |
| 6,398,798 B2 | 6/2002 | Selmon et al. |
| 6,422,736 B1 | 7/2002 | Antonaides et al. |
| 6,425,870 B1 | 7/2002 | Flesch |
| 6,428,551 B1 | 8/2002 | Hall et al. |
| 6,428,552 B1 | 8/2002 | Sparks |
| 6,445,939 B1 | 9/2002 | Swanson et al. |
| 6,447,525 B2 | 9/2002 | Follmer et al. |
| 6,454,727 B1 | 9/2002 | Burbank et al. |
| 6,475,226 B1 | 11/2002 | Belef et al. |
| 6,482,217 B1 | 11/2002 | Pintor et al. |
| 6,497,711 B1 | 12/2002 | Plaia et al. |
| 6,501,551 B1 | 12/2002 | Tearney et al. |
| 6,520,975 B2 | 2/2003 | Branco |
| RE38,018 E | 3/2003 | Anctil et al. |
| 6,532,380 B1 | 3/2003 | Close et al. |
| 6,533,749 B1 | 3/2003 | Mitusina et al. |
| 6,561,998 B1 | 5/2003 | Roth et al. |
| 6,565,588 B1 | 5/2003 | Clement et al. |
| 6,569,177 B1 | 5/2003 | Dillard et al. |
| 6,592,526 B1 | 7/2003 | Lenker |
| 6,605,061 B2 | 8/2003 | VanTassel et al. |
| 6,610,059 B1 | 8/2003 | West, Jr. |

(56) References Cited

U.S. PATENT DOCUMENTS

| | | |
|---|---|---|
| 6,620,180 B1 | 9/2003 | Bays et al. |
| 6,623,437 B2 | 9/2003 | Hinchcliffe et al. |
| 6,623,495 B2 | 9/2003 | Findlay, III et al. |
| 6,627,784 B2 | 9/2003 | Hudson et al. |
| 6,629,953 B1 | 10/2003 | Boyd |
| 6,638,233 B2 | 10/2003 | Corvi et al. |
| RE38,335 E | 11/2003 | Aust et al. |
| 6,652,505 B1 | 11/2003 | Tsugita |
| 6,652,548 B2 | 11/2003 | Evans et al. |
| 6,656,195 B2 | 12/2003 | Peters et al. |
| 6,666,874 B2 | 12/2003 | Heitzmann et al. |
| 6,682,536 B2 | 1/2004 | Vardi et al. |
| 6,790,204 B2 | 9/2004 | Zadno-Azizi et al. |
| 6,790,215 B2 | 9/2004 | Findlay, III et al. |
| 6,818,001 B2 | 11/2004 | Wulfman et al. |
| 6,830,577 B2 | 12/2004 | Nash et al. |
| 6,843,797 B2 | 1/2005 | Nash et al. |
| 6,849,068 B1 | 2/2005 | Bagaoisan et al. |
| 6,863,676 B2 | 3/2005 | Lee et al. |
| 6,911,026 B1 | 6/2005 | Hall et al. |
| 6,932,502 B2 | 8/2005 | Childers et al. |
| 6,935,768 B2 | 8/2005 | Löwe et al. |
| 7,004,173 B2 | 2/2006 | Sparks et al. |
| 7,153,315 B2 | 12/2006 | Miller |
| 7,169,165 B2 | 1/2007 | Belef et al. |
| 7,208,511 B2 | 4/2007 | Williams et al. |
| 7,318,831 B2 | 1/2008 | Alvarez et al. |
| 7,344,546 B2 | 3/2008 | Wulfman et al. |
| 7,388,495 B2 | 6/2008 | Fallin et al. |
| 7,479,148 B2 | 1/2009 | Beaupre |
| 7,488,322 B2 | 2/2009 | Brunnett et al. |
| 7,524,289 B2 | 4/2009 | Lenker |
| 7,526,481 B1 | 4/2009 | Cusson et al. |
| 7,603,166 B2 | 10/2009 | Casscells, III et al. |
| 7,629,829 B2 | 12/2009 | Lee |
| 7,699,790 B2 | 4/2010 | Simpson |
| 7,708,749 B2 | 5/2010 | Simpson et al. |
| 7,713,235 B2 | 5/2010 | Torrance et al. |
| 7,713,279 B2 | 5/2010 | Simpson et al. |
| 7,729,745 B2 | 6/2010 | Maschke |
| 7,734,332 B2 | 6/2010 | Sher |
| 7,753,852 B2 | 7/2010 | Maschke |
| 7,771,444 B2 | 8/2010 | Patel et al. |
| 7,887,556 B2 | 2/2011 | Simpson et al. |
| 7,951,161 B2 | 5/2011 | Bonnette et al. |
| 7,959,634 B2 | 6/2011 | Sennett |
| 7,981,128 B2 | 7/2011 | To et al. |
| 8,007,506 B2 | 8/2011 | To et al. |
| 8,052,704 B2 | 11/2011 | Olson |
| 8,062,316 B2 | 11/2011 | Patel et al. |
| 8,070,762 B2 | 12/2011 | Escudero et al. |
| 8,109,951 B2 | 2/2012 | Mashke |
| 8,142,464 B2 | 3/2012 | Mitusina |
| 8,192,452 B2 | 6/2012 | Moberg |
| 8,208,990 B2 | 6/2012 | Maschke |
| 8,211,025 B2 | 7/2012 | Donaldson et al. |
| 8,236,016 B2 | 8/2012 | To et al. |
| 8,246,640 B2 | 8/2012 | Rosenthal et al. |
| 8,257,375 B2 | 9/2012 | Maschke |
| 8,275,201 B2 | 9/2012 | Rangwala et al. |
| 8,298,147 B2 | 10/2012 | Huennekens et al. |
| 8,328,829 B2 | 12/2012 | Olson |
| 8,361,094 B2 | 1/2013 | To et al. |
| 2001/0031784 A1 | 10/2001 | Petersen et al. |
| 2001/0031981 A1 | 10/2001 | Evans et al. |
| 2002/0007190 A1* | 1/2002 | Wulfman ....... A61B 17/320758 606/167 |
| 2002/0019644 A1 | 2/2002 | Hastings et al. |
| 2002/0055732 A1 | 5/2002 | Wilson |
| 2002/0058904 A1 | 5/2002 | Boock et al. |
| 2002/0177800 A1 | 11/2002 | Bagaoisan et al. |
| 2002/0188307 A1 | 12/2002 | Pintor et al. |
| 2003/0023263 A1 | 1/2003 | Krolik et al. |
| 2003/0039169 A1 | 2/2003 | Ehrfeld et al. |
| 2003/0120295 A1 | 6/2003 | Simpson et al. |
| 2003/0125757 A1 | 7/2003 | Patel et al. |
| 2003/0199747 A1 | 10/2003 | Michlitsch et al. |
| 2004/0049225 A1 | 3/2004 | Denison |
| 2004/0167554 A1 | 8/2004 | Simpson et al. |
| 2004/0193034 A1 | 9/2004 | Wasicek et al. |
| 2004/0210245 A1 | 10/2004 | Erickson et al. |
| 2005/0004594 A1 | 1/2005 | Nool et al. |
| 2005/0042239 A1 | 2/2005 | Lipiecki et al. |
| 2005/0090849 A1 | 4/2005 | Adams |
| 2006/0074442 A1 | 4/2006 | Noriega et al. |
| 2006/0235334 A1 | 10/2006 | Corvi et al. |
| 2007/0049958 A1 | 3/2007 | Adams |
| 2007/0135886 A1 | 6/2007 | Maschke |
| 2007/0167824 A1 | 7/2007 | Lee et al. |
| 2007/0276419 A1 | 11/2007 | Rosenthal |
| 2008/0004645 A1 | 1/2008 | To et al. |
| 2008/0045986 A1 | 2/2008 | To et al. |
| 2008/0051812 A1 | 2/2008 | Schmitz et al. |
| 2008/0125799 A1 | 5/2008 | Adams |
| 2008/0161840 A1 | 7/2008 | Osiroff et al. |
| 2008/0177139 A1 | 7/2008 | Courtney et al. |
| 2008/0208227 A1 | 8/2008 | Kadykowski et al. |
| 2008/0249553 A1 | 10/2008 | Gruber et al. |
| 2008/0312673 A1 | 12/2008 | Viswanathan et al. |
| 2009/0012548 A1 | 1/2009 | Thatcher et al. |
| 2009/0018565 A1 | 1/2009 | To et al. |
| 2009/0018566 A1 | 1/2009 | Escudero et al. |
| 2009/0048602 A1 | 2/2009 | O'Donoghue |
| 2009/0138031 A1 | 5/2009 | Tsukernik |
| 2009/0187203 A1 | 7/2009 | Corvi et al. |
| 2009/0216180 A1 | 8/2009 | Lee et al. |
| 2009/0275966 A1 | 11/2009 | Mitusina |
| 2009/0306689 A1 | 12/2009 | Welty et al. |
| 2010/0030216 A1 | 2/2010 | Arcenio |
| 2010/0130996 A1 | 5/2010 | Doud et al. |
| 2010/0312263 A1 | 12/2010 | Moberg et al. |
| 2011/0004107 A1 | 1/2011 | Rosenthal et al. |
| 2011/0130777 A1* | 6/2011 | Zhang ........... A61B 17/320783 606/159 |
| 2011/0144673 A1 | 6/2011 | Zhang et al. |

FOREIGN PATENT DOCUMENTS

| | | |
|---|---|---|
| DE | 8900059 U1 | 5/1989 |
| DE | 9303531 U1 | 7/1994 |
| DE | 4444166 A1 | 6/1998 |
| DE | 29722136 U1 | 4/1999 |
| EP | 0107009 A2 | 5/1984 |
| EP | 0229620 A2 | 7/1987 |
| EP | 0330843 A1 | 9/1989 |
| EP | 0431752 A2 | 6/1991 |
| EP | 0514810 A1 | 11/1992 |
| EP | 1767159 A1 | 3/2007 |
| GB | 2093353 A | 9/1982 |
| GB | 2115829 A | 9/1983 |
| JP | 1200459 A | 7/1992 |
| JP | 5042162 A | 2/1993 |
| JP | 5056984 A | 3/1993 |
| SU | 442795 A1 | 9/1974 |
| SU | 665908 A1 | 6/1979 |
| WO | 9746164 A1 | 12/1997 |
| WO | 9824372 A1 | 6/1998 |
| WO | 0054735 A1 | 9/2000 |
| WO | 0062913 A1 | 10/2000 |
| WO | 0072955 A1 | 12/2000 |
| WO | 0115609 A1 | 3/2001 |
| WO | 0119444 A1 | 3/2001 |
| WO | 0130433 A1 | 5/2001 |
| WO | 2010/126882 A1 | 11/2010 |

OTHER PUBLICATIONS

Brezinski et al., "Optical Coherence Tomography for Optical Biopsy," Circulation, 93:1206-1213 (1996).

Brezinski et al., "Assessing Atherosclerotic Plaque Morphology: Comparison of Optical Coherence Tomography and High Frequency Intravascular Ultraound," Heart, 77:397-403 (1997).

(56) References Cited

OTHER PUBLICATIONS

Huang et al., "Optical Coherence Tomography," Science, 254:1178-1181 (1991).

Amplatz Coronary Catheters, posted: Feb. 25, 2009, [online], [retrieved on Mar. 29, 2011], retrieved from the Cardiophile MD using Internet website <URL:http://cardiophile.org/2009/02/amplatzcoronary-catheter.html> (2 pages).

Judkins Left Coronary Catheter, posted: Feb. 19, 2009, [online], [retrieved on Mar. 29, 2011], retrieved from the Cardiophile MD using Internet website <URL:http://cardiophile.org/2009/02/judkins-left-coronary-catheter.html> (2 pages).

\* cited by examiner

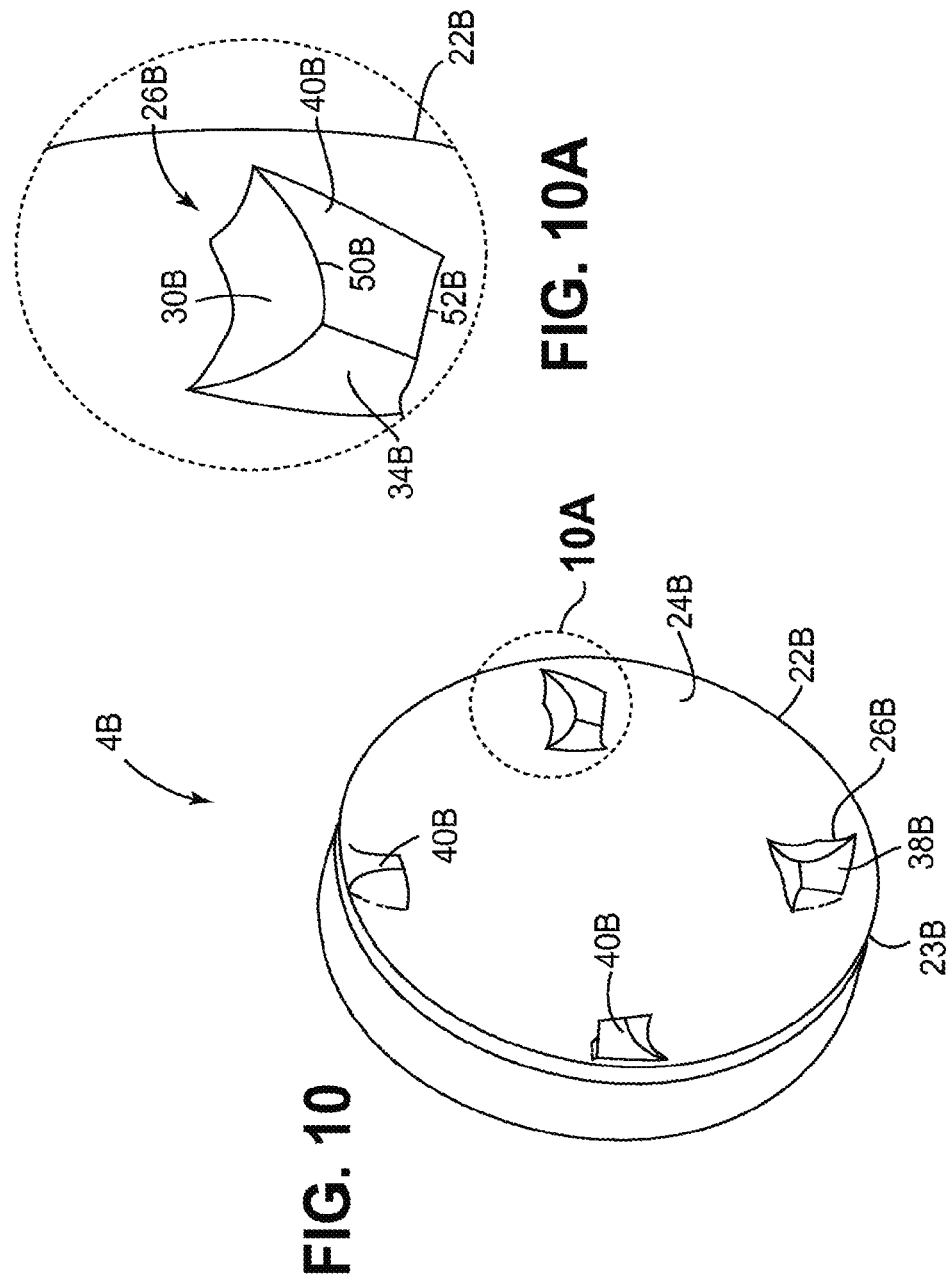

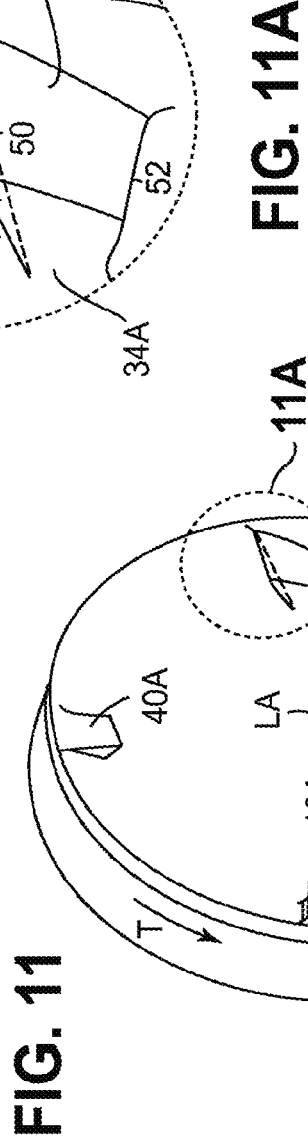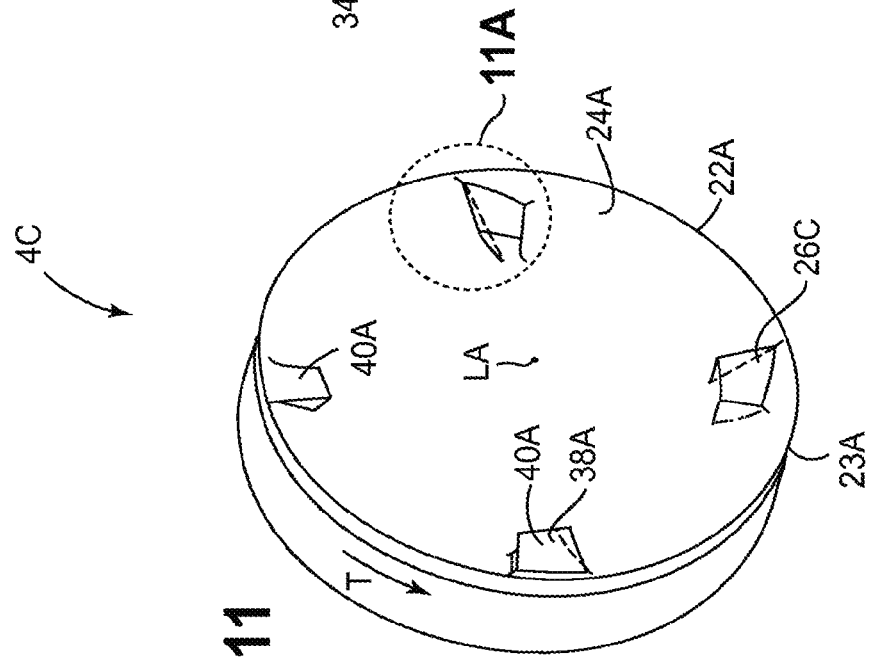

TISSUE-REMOVING CATHETER WITH ROTATABLE CUTTER

CROSS-REFERENCE TO RELATED APPLICATION

This application is a continuation of U.S. application Ser. No. 13/671,695, filed Nov. 8, 2012, the entire contents of which are incorporated herein by reference.

FIELD OF THE DISCLOSURE

The present invention generally relates to tissue-removing catheter with a rotatable cutter.

BACKGROUND

Catheters are used to remove unwanted tissue from the body. As an example, atherectomy catheters are used to remove material from a blood vessel to open the blood vessel and improve blood flow through the vessel.

SUMMARY

In one aspect, a tissue-removing catheter generally comprises an elongate catheter body having opposite distal and proximal portions and being sized and shaped for introduction into a body lumen of a subject. A drive shaft extends longitudinally within the catheter body. The drive shaft is rotatable relative to the catheter body about a longitudinal axis of the drive shaft. A cutting element at the distal portion of the elongate catheter body has opposite proximal and distal ends and a longitudinal axis extending therebetween. The cutting element is operatively connected to the drive shaft for rotation about a longitudinal axis of the cutting element. The cutting element includes an annular cutting edge at the distal end of the cutting element surrounding the longitudinal axis of the cutting element. The annular cutting edge has a radius as taken from the longitudinal axis of the cutting element. An inner surface of the cutting element extends proximally from the cutting edge and defines an internal cavity. At least one raised element in the internal cavity of the cutting element extends generally longitudinally outward from the inner surface. The at least one raised element includes a leading radial wall extending generally radially inward toward the longitudinal axis of the cutting element. The leading radial wall has a radially outermost portion relative to the longitudinal axis of the cutting element, a radially innermost portion relative to the longitudinal axis of the cutting element, and a radial length extending between the radially outermost and innermost portions. The radially innermost portion of the leading radial wall is spaced a radial distance from the longitudinal axis that is less than 66% of the radius of the annular cutting edge.

In another aspect, a tissue-removing catheter generally comprises an elongate catheter body having opposite distal and proximal portions and being sized and shaped for introduction into a body lumen of a subject. The catheter body has a window at the distal portion thereof. A drive shaft extends longitudinally within the catheter body. The drive shaft is rotatable relative to the catheter body about a longitudinal axis of the drive shaft. A cutting element at the distal portion of the elongate catheter body is adjacent the window. The cutting element has opposite proximal and distal ends and a longitudinal axis extending therebetween, the cutting element being operatively connected to the drive shaft for rotation about the longitudinal axis of the cutting element. The cutting element includes an annular cutting edge at the distal end of the cutting element surrounding the longitudinal axis of the cutting element, the annular cutting edge having a radius as taken from the longitudinal axis of the cutting element. An inner surface of the cutting element extends proximally from the cutting edge and defining an internal cavity. At least one raised element in the internal cavity has leading radial wall extending generally radially inward toward the longitudinal axis of the cutting element. The cutting element is extendable through the window during operation such that as the cutting element is being rotated about its longitudinal axis, less than an entire radial portion of the leading radial wall passes through the window.

In another aspect, a tissue-removing catheter generally comprises an elongate catheter body having opposite distal and proximal portions and being sized and shaped for introduction into a body lumen of a subject. A drive shaft extends longitudinally within the catheter body, wherein the drive shaft is rotatable relative to the catheter body about a longitudinal axis of the drive shaft. A cutting element at the distal portion of the elongate catheter body has opposite proximal and distal ends and a longitudinal axis extending therebetween. The cutting element is operatively connected to the drive shaft for rotation about a longitudinal axis of the cutting element. The cutting element includes an annular cutting edge at the distal end of the cutting element surrounding the longitudinal axis of the cutting element. The annular cutting edge has a radius as taken from the longitudinal axis of the cutting element. An inner surface extends proximally from the cutting edge and defining an internal cavity. At least one raised element in the internal cavity extends generally longitudinally outward from the inner surface. The at least one raised element includes a leading radial wall extending generally radially inward toward the longitudinal axis of the cutting element. The leading radial wall has a radially outermost portion relative to the longitudinal axis of the cutting element, a radially innermost portion relative to the longitudinal axis of the cutting element, and a radial length extending between the radially outermost and innermost portions. The radially outermost portion is spaced apart radially from the inner surface of the cutting element.

Other features will be in part apparent and in part pointed out hereinafter.

BRIEF DESCRIPTION OF THE DRAWINGS

FIG. 10 is a perspective of the embodiment of the cutting element illustrated in FIG. 9;

FIG. 10A is an enlarged detail of FIG. 10 showing of the raised elements of the cutting element embodiment;

FIG. 11 is perspective of a modified version of the embodiment of the cutting element illustrated in FIG. 8;

FIG. 11A is an enlarged detail of FIG. 11 showing one of the raised elements;

Corresponding reference characters indicate corresponding parts throughout the drawings.

DETAILED DESCRIPTION OF THE DRAWINGS

Figure 1:
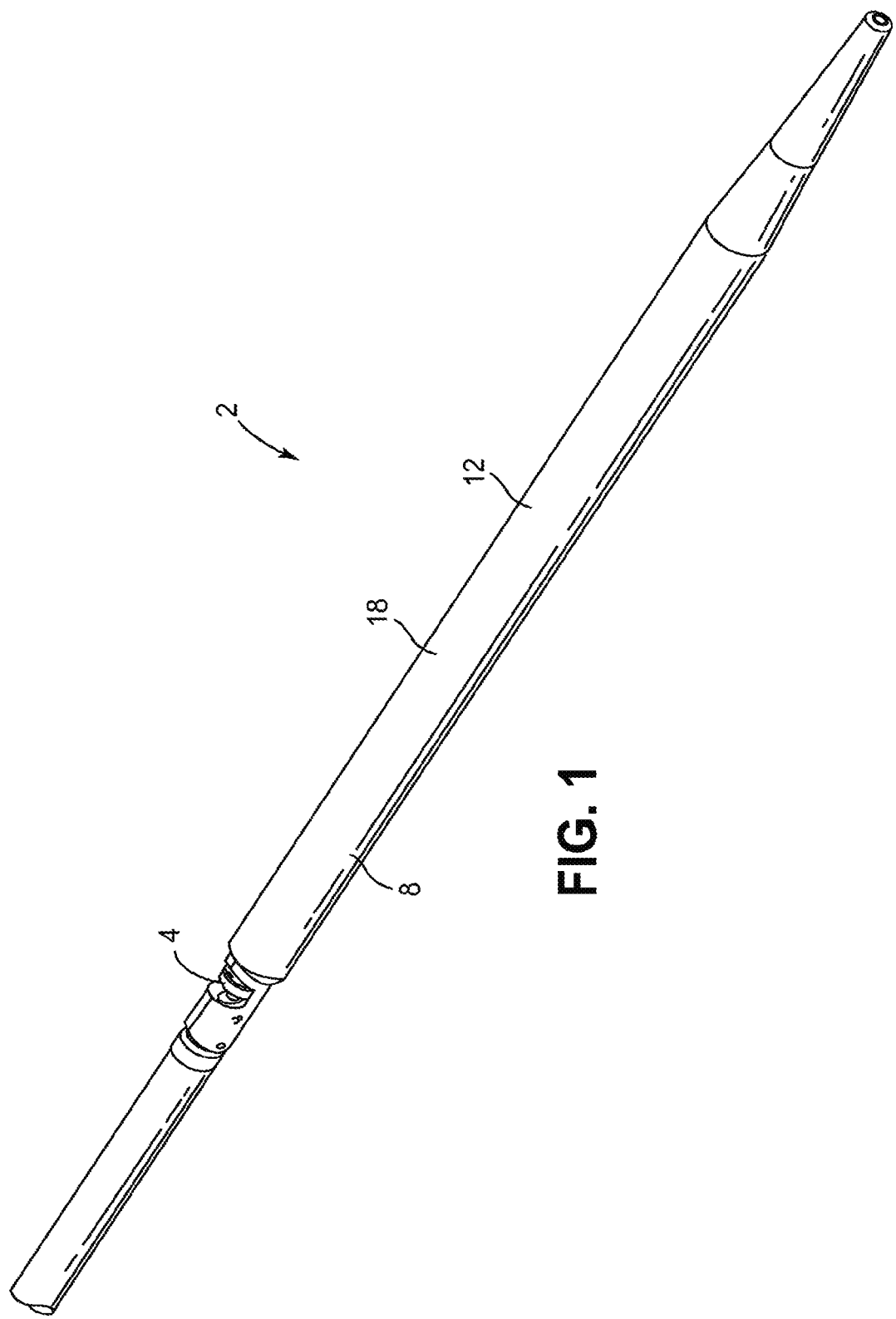
FIG. 1 is a perspective of a distal end of an atherectomy catheter.

Referring now to the drawings, several embodiments of a tissue-removing catheter for removing tissue from a body lumen are disclosed. In particular, the illustrated catheter embodiments are suitable for removing tissue from a body lumen wall, and are particularly suitable for removing (i.e., excising) plaque tissue from a vessel wall (e.g., peripheral arterial or peripheral venous wall). Features of the disclosed embodiments, however, may also be suitable for treating chronic total occlusion (CTO) of blood vessels, particularly peripheral arteries, and stenoses of other body lumens and other hyperplastic and neoplastic conditions in other body lumens, such as the ureter, the biliary duct, respiratory passages, the pancreatic duct, the lymphatic duct, and the like. Neoplastic cell growth will often occur as a result of a tumor surrounding and intruding into a body lumen. Removal of such material can thus be beneficial to maintain patency of the body lumen. While the remaining discussion is directed toward catheters for removing tissue from and penetrating occlusions in blood vessels (e.g., atheromatous or thrombotic occlusive material in an artery, or other occlusions in veins), it will be appreciated that the teachings of the present disclosure apply equally to other types of tissue-removing catheters, including, but not limited to, catheters for penetrating and/or removing tissue from a variety of occlusive, stenotic, or hyperplastic material in a variety of body lumens.

Referring to FIGS. 1 to 4, an atherectomy catheter 2, which has a cutting element 4, which is used to cut material from a blood flow lumen. The catheter has an elongate body 8 having distal and proximal portions and being sized and shaped for insertion into a body lumen of a subject. The cutting element 4 is movable between a stored position (FIG. 2) and a cutting position (FIG. 3) relative to a window or opening 6 in the catheter body 8 adjacent the distal portion. The cutting element 8 moves outwardly relative to the opening 6 so that an exposed portion of the element 4 extends outside the body 8 through the opening 6. The cutting element 4 may be positioned relative to the body 8 and opening 6 so that less than 90 degrees of the cutting element 4 is exposed to cut tissue. Of course, more of the cutting element 4 may be exposed without departing from numerous aspects of the invention.

Catheter 2 may have a maximum size of 3, 4, 5, 6, 7, 8, 9, 10, or 12 French (1, 1.3, 1.7, 2, 2.3, 2.7, 3, 3.3, or 4 mm) and may have a working length ranging of 20, 30, 40, 60, 80, 100, 120, 150, 180 or 210 cm depending on the requirements of the anatomical location in which use of the catheter is contemplated. Cutter 4 preferably has a diameter slightly less than that of the maximum size of catheter 2, typically 0.010" (0.025 cm), 0.015" (0.038 cm), 0.020" (0.051 cm), 0.025" (0.064 cm) or 0.030" (0.076 cm) less. However these relative dimensions are not meant to be limiting.

The catheter 2 is moved distally through a vessel with the cutting element 4 in the working or cutting position as described in further detail below. As the catheter 2 moves through the blood vessel, the tissue is cut by the cutting element 4 and is directed into a tissue chamber 12 positioned distal to the cutting element 4. The tissue chamber 12 may be somewhat elongate to accommodate the tissue that has been cut.

The cutting element 4 is moved proximally from the stored position so that a cam surface 14 on the cutting element 4 engages a ramp 16 on the body 8 of the catheter 2. The interaction between the cam surface 14 and the ramp 16 causes the cutting element 4 to move to the cutting position and also causes a tip 18 to deflect which tends to move the cutting element 4 toward the tissue to be cut.

The cutting element 4 is coupled to a drive shaft 20 that extends through a lumen 21 in the catheter 2. The cutting element 4 is rotated about a longitudinal axis LA when the drive shaft rotates about its longitudinal axis. The cutting element 4 is rotated at about 1 to 160,000 rpm but may be rotated at any other suitable speed depending upon the particular application.

Figure 2:
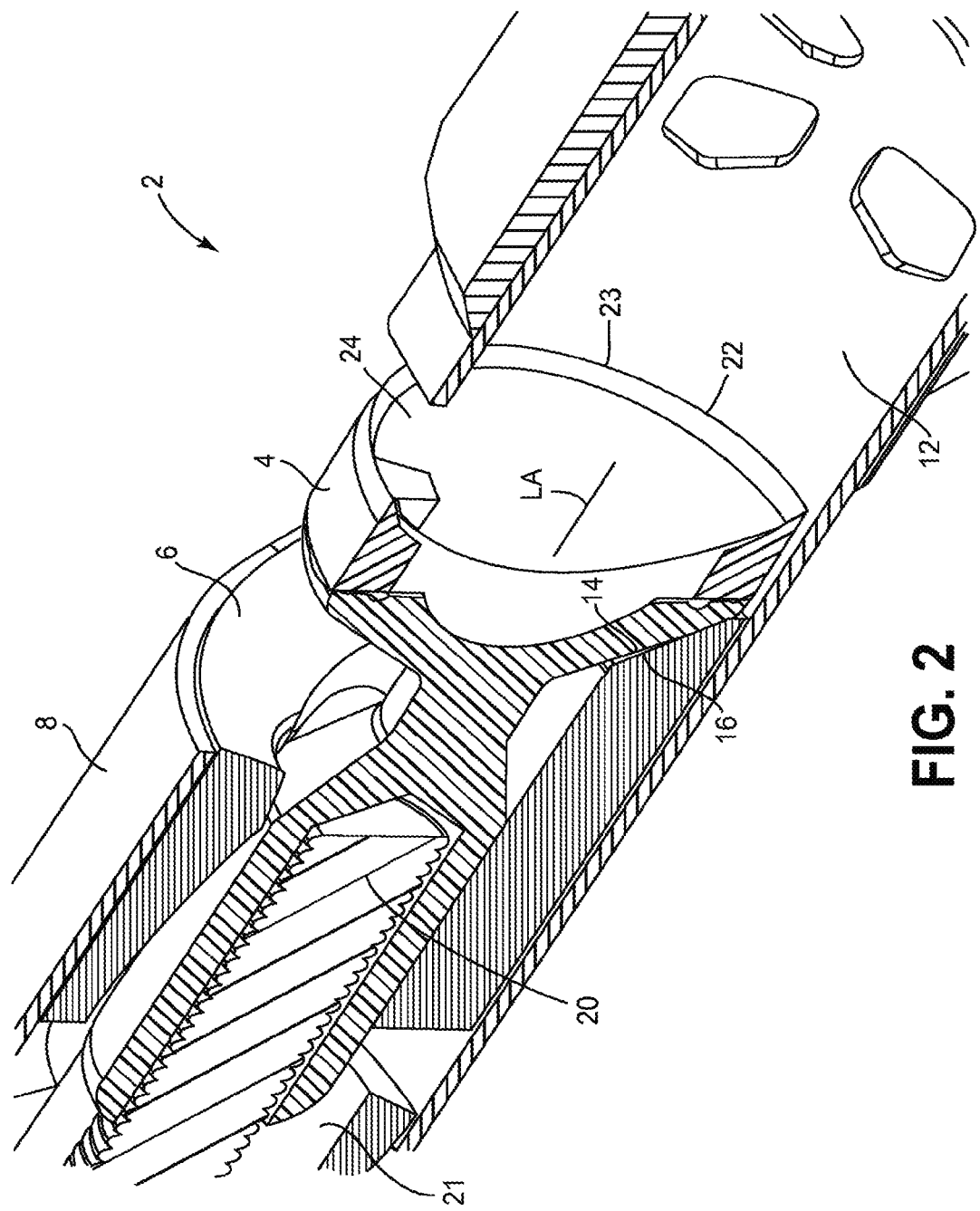
FIG. 2 is an enlarged fragmentary section of the atherectomy catheter of FIG. 1 with a cutting element in a stowed position.
Figure 3:
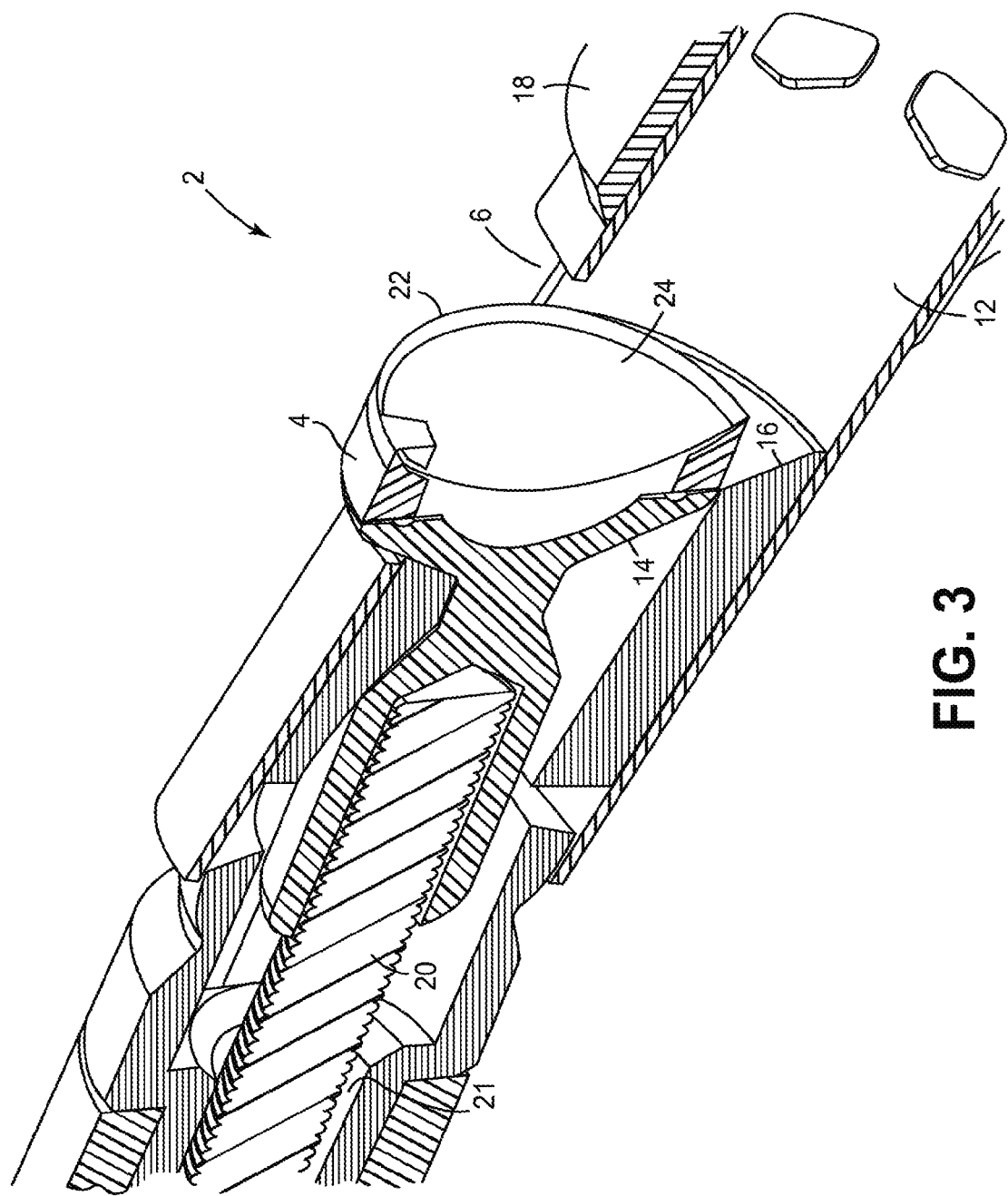
FIG. 3 is the enlarged fragmentary section of FIG. 1 but with a cutting element in a working position.
Figure 4:
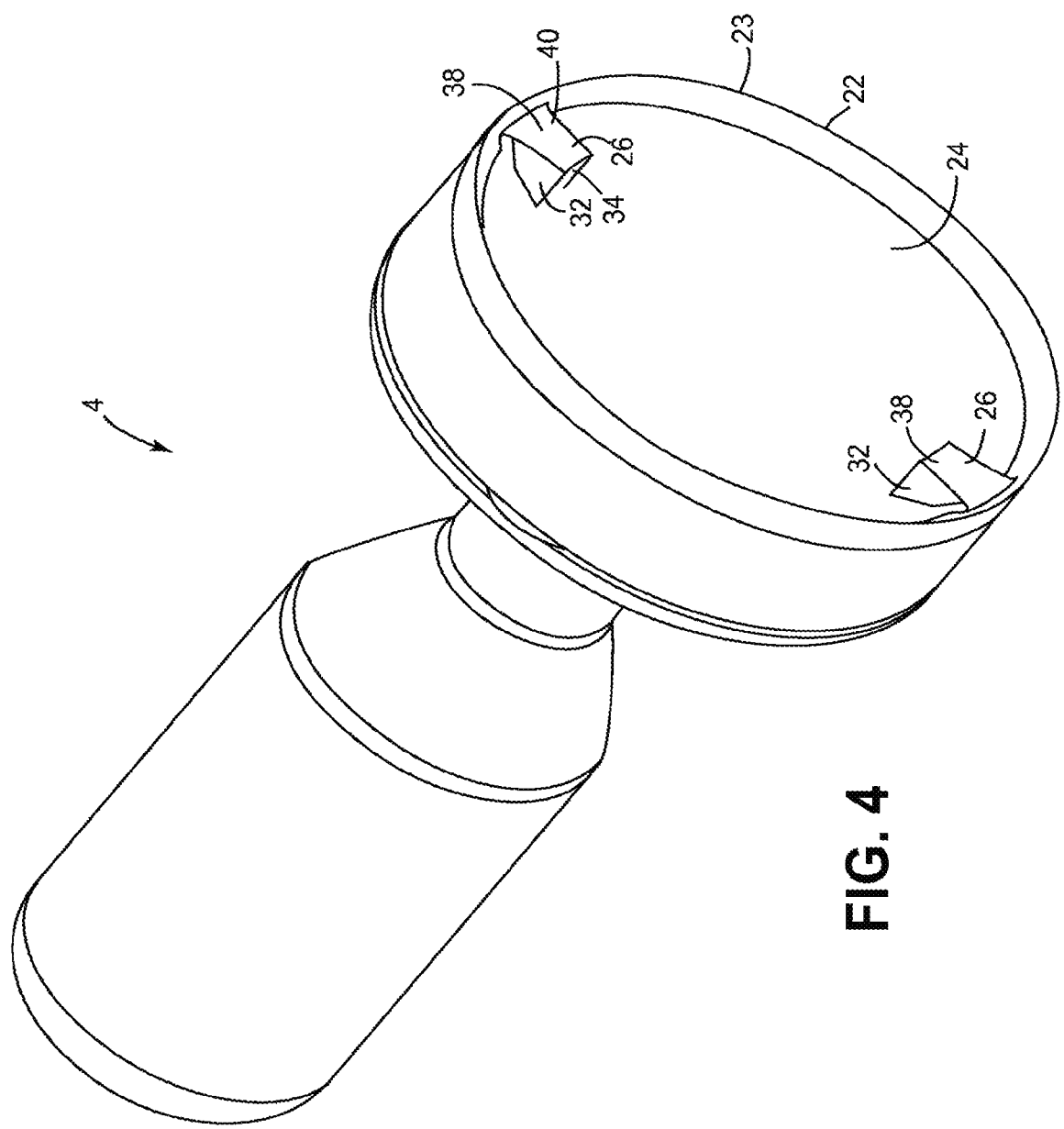
FIG. 4 is a perspective of an embodiment of a cutting element.
Figure 5:
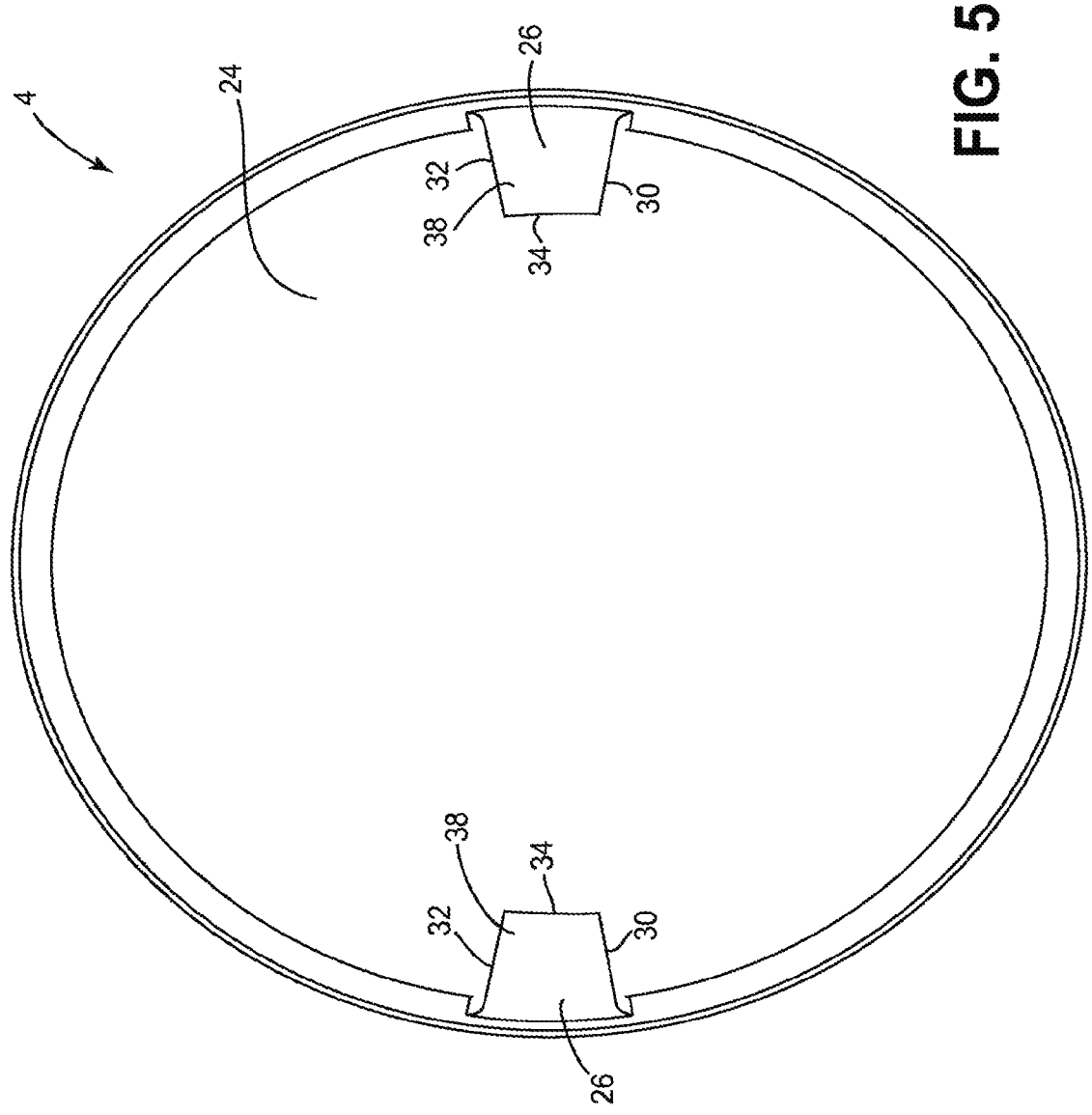
FIG. 5 is an enlarged end view of the cutting element.

Referring to FIGS. 2, 4 and 5, the cutting element 4 is shown. The term "along the longitudinal axis" as used herein shall mean the view of FIG. 5 that shows the distal end of the cutting element 4 when viewed in the direction of the longitudinal axis and/or the axis of rotation. The cutting element 4 has an annular cutting edge 22 that may be a continuous, uninterrupted, circular-shaped edge although it may also include ridges, teeth, serrations or other features without departing from the scope of the invention. The cutting edge 22 may be at a radially outer edge 23 of the cutting element 4 when the cutting element 4 is in the cutting position. A circumferential inner surface 25 of the cutting element 4 extends from the cutting edge 22 and is chamfered or beveled.

The cutting element 4 has an inner cup-shaped surface 24, which directs the tissue cut by the cutting edge 22 into the tissue chamber 12. In the illustrated embodiment, the circumferential inner surface 25 and the inner cup-shaped surface 24 define an internal cavity of the cutting element 4. The cup-shaped surface 24 may be a smooth and continuous surface free of through-holes, teeth, fins or other features, which disrupt the smooth nature of the surface 24 for at least half the distance from the longitudinal axis LA to the outer radius at the cutting edge 22. The cup-shaped surface 24 may also be free of any such features throughout an area of at least 300 degrees relative to the longitudinal axis LA.

Cutter 4 may be comprised of steel, tungsten carbide, tungsten carbide cobalt, tungsten carbide molybdenum, silicon carbide, silicon nitride, ceramic, amorphous metals or other materials and may be manufactured by methods including turning, grinding, sintering, electro-discharge machining (EDM), laser cutting, heat treating, precipitation hardening, casting or other methods.

Figure 6:
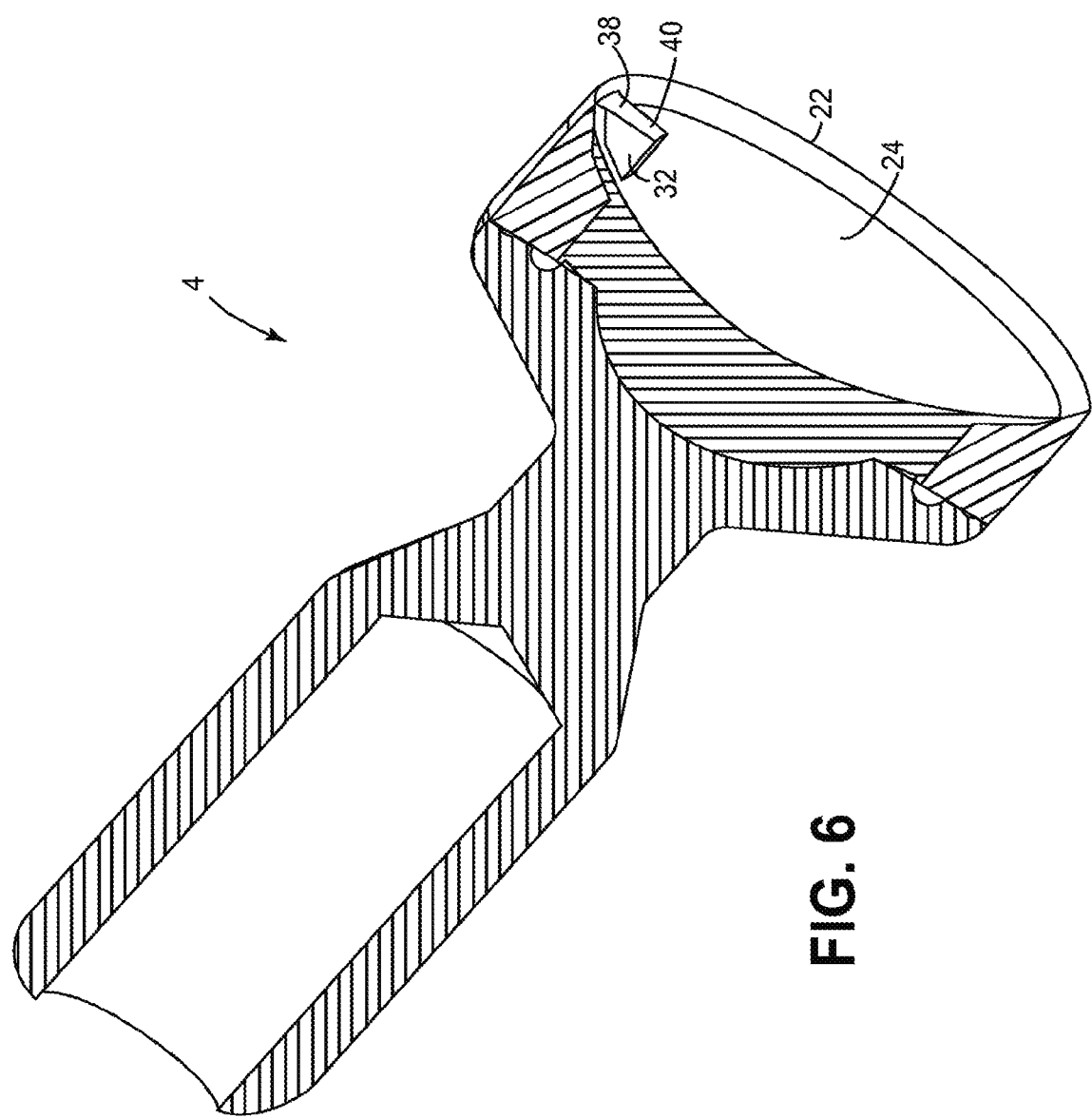
FIG. 6 is a longitudinal section of the cutting element of FIG. 4.

Referring to FIGS. 4 to 6, one or more raised elements 26 extend outwardly from the cup-shaped surface 24 with FIG. 5 showing two raised elements 26. The raised element 26 is a small wedge of material that rises relatively abruptly from the cup-shaped surface 24. The raised element 26 has a first wall 30 and a second wall 32 that both extend radially and form an angle of about 20 degrees therebetween so that the two raised elements 26 together occupy an area of about 40 degrees and altogether may be less than 60 degrees. A third wall 34 extends between the radially inner portion of the first and second walls 30, 32. The raised element 26 helps to break up hard tissue and plaque by applying a relatively blunt force to the hard tissue or plaque since cutting such tissue with the cutting edge 22 is often not effective.

The raised elements 26 altogether occupy a relatively small part of the cup-shaped surface 24. The raised elements 26 together may occupy less than 5% of a surface area of the cutting element 4. The term "surface area of the cutting element" as used herein shall mean the surface area which is radially inward from the outer or cutting edge 22 and is exposed when viewed along the longitudinal axis LA. Stated another way, at least 95% of the surface area of the cutting element is a smooth cup-shaped surface when viewed along the longitudinal axis. However, the raised element surface area may occupy more of the total surface area of the cup. By sizing and positioning the raised element 26 in this manner, the raised element 26 does not interfere with the ability of the cutting element 4 to cut and re-direct tissue into the tissue chamber while still providing the ability to break up hard tissue and plaque with the raised element 26.

The raised element 26 may be recessed from the cutting edge 22 longitudinally and/or radially. The raised element 26 may be recessed longitudinally (along axis LA) from the cutting edge 0.0010 to 0.0020 inch (0.0025 to 0.0051 cm) and may be recessed about 0.0015 inch (0.0038 cm). The raised element 26 may be recessed radially from the cutting edge 22 by about the same amount. A distal wall 38 of the cutting element 4 forms a flat surface 40, which is perpendicular to the longitudinal axis LA so that the entire surface is recessed the same distance from the cutting edge. The distal wall 38 may take any other shape, such as a curved shape, or may be tilted, inclined or beveled as now described. The raised element may have other shapes, sizes and locations within the scope of the present invention.

Figure 7:
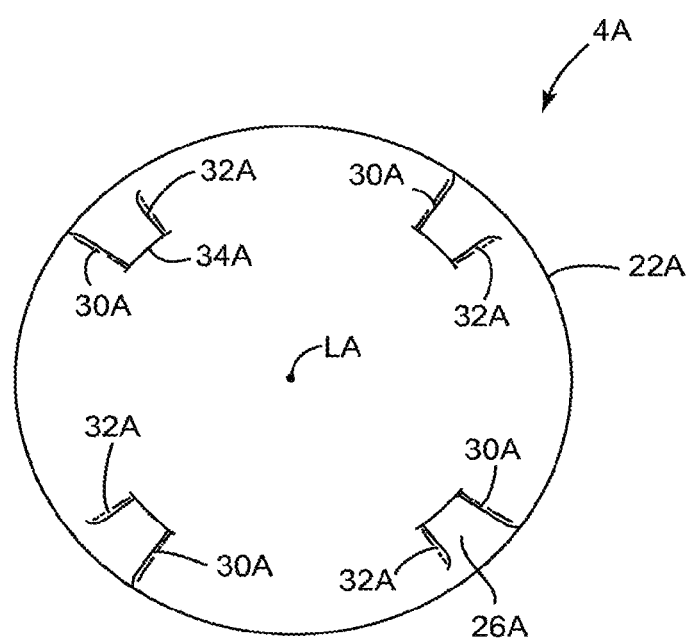
FIG. 7 is an end view of another embodiment of a cutting element, which may be used with the atherectomy catheter shown in FIG. 1.
Figure 8A:
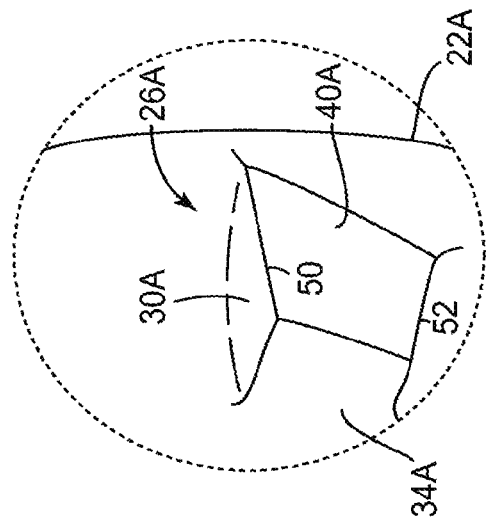
FIG. 8A is an enlarged detail of FIG. 8 showing one of the raised elements of the cutting element.
Figure 8:
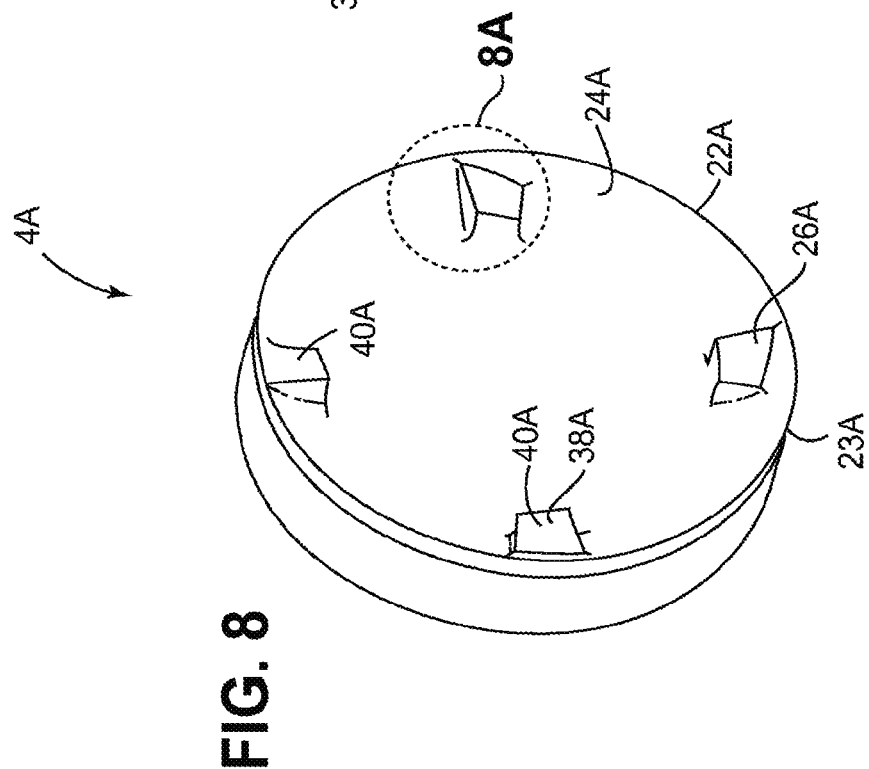
FIG. 8 is a perspective of the cutting element of FIG. 7.

Referring to FIGS. 7, 8 and 8A, another cutting element 4A is shown wherein the same or similar reference numbers refer to the same or similar structure and all discussion concerning the same or similar features of the cutting element 4 are equally applicable here unless noted otherwise. The cutting element 4A has a cutting edge 22A that may be a continuous, uninterrupted, circular-shaped edge although it may also include ridges, teeth, serrations or other features without departing from the scope of the invention. The cutting edge 22A may be at a radially outer edge 23A of the cutting element 4A when the cutting element 4A is in the cutting position. The cutting element 4A has a cup-shaped surface 24A that directs the tissue cut by the cutting edge 22A into the tissue chamber 12 (see FIG. 2). The cup-shaped surface 24A may be a substantially smooth and continuous surface as described above in connection with the cutting element 4.

One or more raised elements 26A extend outwardly from the cup-shaped surface 24A. FIG. 8 shows four raised elements 26A but may include any number such as 1, 2, 3, 4, 6 or 8 raised elements. The raised element 26A is a small wedge of material that rises relatively abruptly from the cup-shaped surface 24A. The raised element 26A has a first wall 30A and a second wall 32A which, in one embodiment, both extend radially and form an angle of about 1 to 30 degrees therebetween so that the four raised elements 26A together occupy an area of about 4 to 60 degrees and altogether may be less than 60 degrees. A third wall 34A extends between the radially inner portion of the first and second walls 30A, 32A. In some embodiments the raised elements 26A may occupy a relatively small part of the cup-shaped surface 24A and may be recessed from the cutting edge 22A in the manner described above in connection with the cutting element 4. In other embodiments at least 60%, 70%, 80% or 90% of the surface area of the cutting element is a smooth cup-shaped surface.

A distal wall 38A of the cutting element 4A has a surface 40A that forms an angle of about 30 to 90 degrees with respect to the longitudinal axis LA. The entire surface 40A may still be somewhat close to but recessed from the cutting edge 22A so that the entire surface 40A is at least 0.0010, 0.0020, 0.0030, 0.0040 or 0.0050 inches (0.0025, 0.0051, 0.0076, 0.0101, or 0.0127 cm) from the cutting edge. A leading edge 50 formed at the intersection of wall 30A and distal wall 38A is closer to the cutting edge 22A than an edge 52 formed at the intersection of wall 32A and distal wall 38A. The cutting element 4A may be rotated in either direction so that the raised edge 50 may be the leading or trailing edge. In some embodiments the raised edge may be 0.0010 to 0.0020 inch (0.0025 to 0.0051 cm) from the cutting edge. The raised elements 26A may all be formed in the same manner or may be different from one another. For example, some of the elements 26A could be angled in different directions so that two of the elements have the raised edge 50 as the leading edge and two of the elements 26A have the raised edge 50 as the trailing edge. The raised elements 26A may also subtend different angles, be of different heights or may have different radial lengths without departing from various aspects of the present invention.

Figure 9:
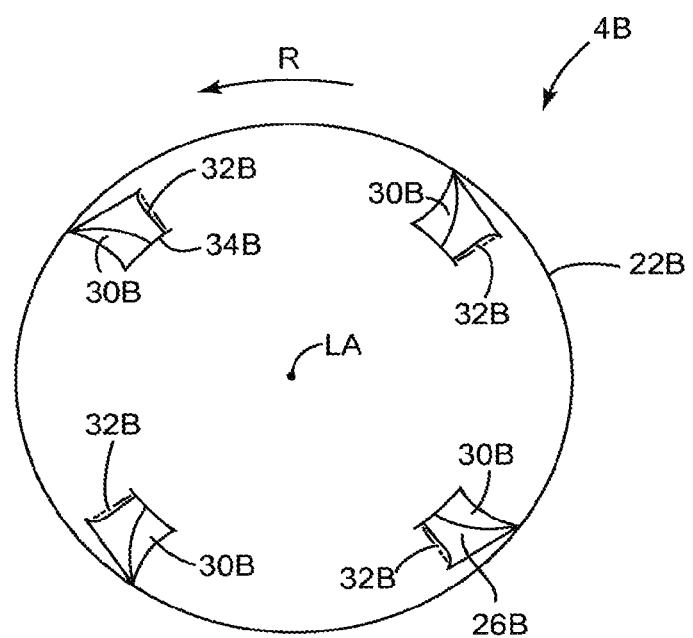
FIG. 9 is an end view of another embodiment of a cutting element, which may be used with the atherectomy catheter shown in FIG. 1.
Figure 12:
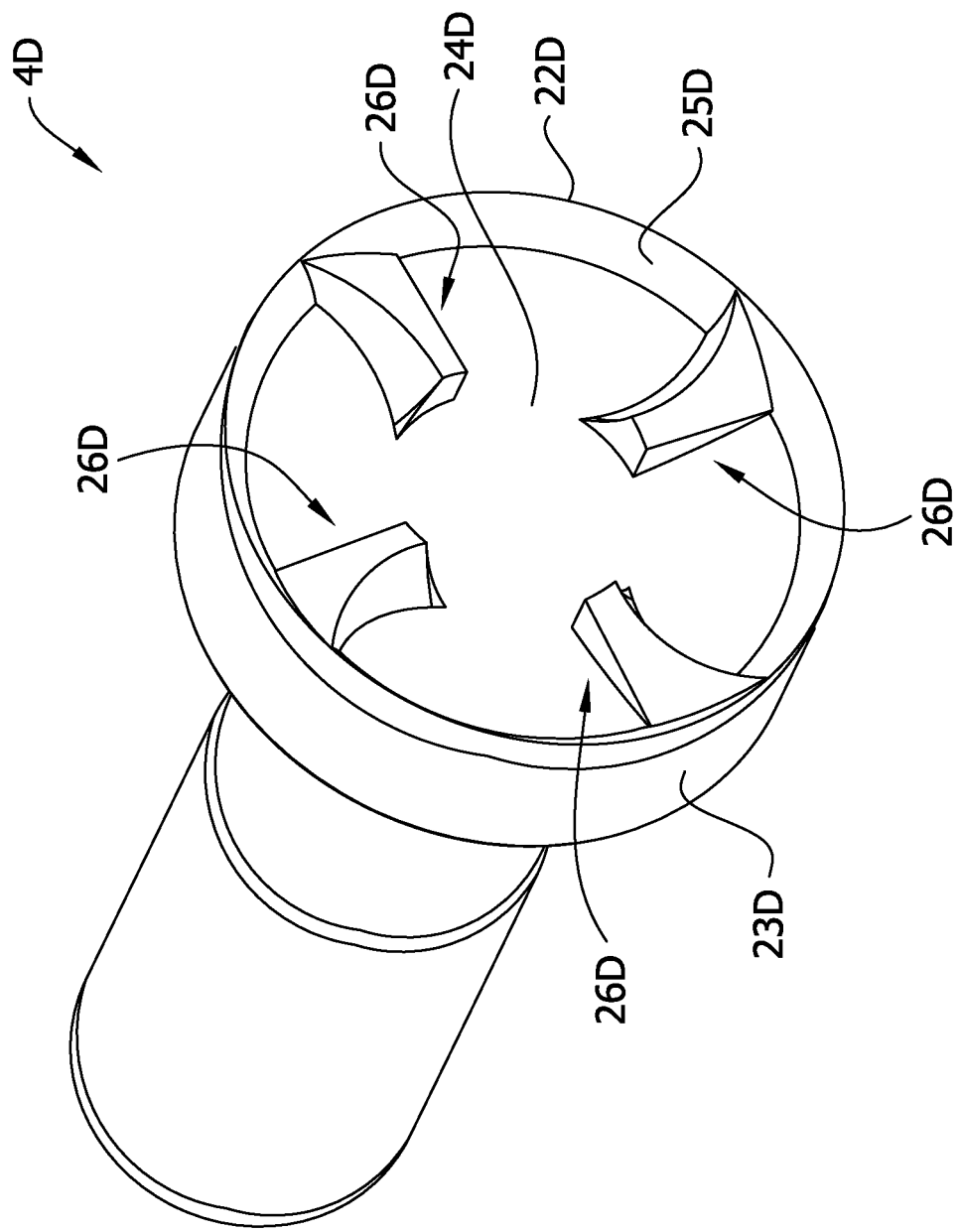
FIG. 12 is a perspective of another embodiment of a cutting element.

Referring to FIGS. 9, 10 and 10A, another cutting element 4B is shown wherein the same or similar reference numbers refer to the same or similar structure and all discussion concerning the same or similar features of the cutting element 4 are equally applicable here unless noted otherwise. The cutting element 4B has a cutting edge 22B that may be a continuous, uninterrupted, circular-shaped edge although it may also include ridges, teeth, serrations or other features without departing from the scope of the invention. The cutting edge 22B may be at a radially outer edge 23B of the cutting element 4B when the cutting element 4B is in the cutting position. The cutting element 4B has a cup-shaped surface 24B that directs the tissue cut by the cutting edge 22B into the tissue chamber 12 (see FIG. 2). In one embodiment the cup-shaped surface 24B may be a substantially smooth and continuous surface as described above in connection with the cutting element 4.

One or more raised elements 26B, extend outwardly from the cup-shaped surface 24B. FIGS. 9 and 10 show four raised elements 26B but may include any number such as 1, 2, 3, 4, 6 or 8 raised elements. The raised element 26B is a small wedge of material that rises relatively abruptly from the cup-shaped surface 24B and which subtends an arc of about 1 to 30 degrees relative to axis LA, the four raised elements 26B subtending an arc of about 4 to 60 degrees altogether. The raised element 26B has a first wall 30B that extends between a curved leading edge 50B and cup-shaped surface 24B and also has a second wall 32B which extends radially relative to axis LA. A third wall 34B extends between the radially inner portion of the first and second walls 30B, 32B. In some embodiments the raised elements 26B may occupy a relative small part of the cup-shaped surface 24B and may be recessed from the cutting edge 22B in the manner described above in connection with the cutting element 4. In other embodiments at least 60%, 70%, 80% or 90% of the surface area of the cutting element is a smooth cup-shaped surface.

A distal wall 38B of the cutting element 4B has a surface 40B that forms an angle of less than 90 degrees with respect to the longitudinal axis LA. In some embodiments the surface 40B is angled such that edge 50B is more distal than edge 52B. The entire surface 40B may still be somewhat close to but recessed from the cutting edge 22B so that the entire surface 40B is from 0.0010 to 0.0050 inch (0.0025 to 0.0127 cm), including 0.0010, 0.0020, 0.0030, 0.0040 or 0.0050 inch (0.0025, 0.0051, 0.0076, 0.0101, or 0.0127 cm), from the cutting edge. An edge 50B formed at the intersection of wall 30B and distal wall 38B is closer to the cutting edge 22B than an edge 52B formed at the intersection of wall 32B and distal wall 38B. The included angle between wall 30B and surface 40B, in the vicinity of edge 50B, is greater than 90 degrees. The cutting element 4B may be rotated in either direction so that the raised edge 50B may be the leading or trailing edge. In one embodiment, the cutter 4B is rotated in the direction of arrow R so that edge 50B is the leading edge. Raised edges 50B, 52B may be 0.0010 to 0.0020 inch (0.0025 to 0.0051 cm) from the cutting edge. The raised elements 26B may all be formed in the same manner or may be different from one another. For example, some of the elements 26B could be angled in different directions so that two of the elements have the raised edge 50B as the leading edge and two of the elements 26A have the raised edge 50B as the trailing edge. The raised elements 26B may also subtend different angles, be of different heights or may have different radial lengths without departing from various aspects of the present invention.

In one embodiment cutter 4B is rotated in the direction of arrow R and pushed distally to force cup-shaped surface 24B and raised elements 26B into contact with material such as atheroma or plaque. Raised elements 26B will tend to concentrate cutting force along edge 50B due to relief angle between cutter axis LA and surface 40B. Cutter 4B will tend to scrape away material such as atheroma or plaque rather than cut into this material due to the obtuse included angle between wall 30B and surface 40B, in the vicinity of edge 50B. Material contacted by raised elements 26B will tend to be directed toward axis LA by surface 30B which curves from a relatively tangential angle near edge 22B to a relatively radial angle near edge 34B.

Referring to FIGS. 11 and 11A, another cutting element 4C is shown. Cutting element 4C is a modified version of cutting element 4A. The modification consists of adding an undercut 41C to the leading face of one or more raised element 26A, resulting in modified raised element 26C. When cutter 4C is rotated in the direction of arrow T the undercut directs particles of material into the concave cavity defined by cup-shaped surface 24A of the cutter, and towards axis LA of the cutter. Optionally an undercut can be applied to the leading face of one or more raised element 26, 26B of cutting elements 4, 4B respectively as well as to one or more raised elements 26A of cutting element 4A.

Undercut 41C is defined by wall 30C which is oriented at an acute angle to surface 40A, which intersects cup-shaped surface 24A, and which meets wall 34A. The plane of wall 30C also intersects axis LA at less than 5, 10, 15, or 20 degrees such that, when cutter 4C is spinning in direction T, particles of material tend to travel along wall 30C in directions away from cutting edge 22A and toward axis LA. In some embodiments wall 43C may be interspersed between the intersection of wall 30C and wall 40A. Wall 43C may be oriented at any desired rake angle, such as for example a negative rake angle where the raised element will tend to not dig in to material being cut.

Referring to FIGS. 12-18, another embodiment of a cutting element is indicated generally at 4D. The cutting element 4D is similar to cutting element 4B, except that, as explained below, radial lengths of the raised elements, generally indicated at 26D, are greater than radial lengths of the raised elements 26B of the cutting element 4B. The cutting element 4D has an annular cutting edge 22D that may be a continuous, uninterrupted, arcuate-shaped edge although it may also include ridges, teeth, serrations or other features without departing from the scope of the invention. In the illustrated embodiment, an inner surface of the cutting element 4D defines an internal cavity of the cutting element. The inner surface includes a circumferential inner surface 25D, which is chamfered or beveled, extending from the cutting edge 22, and a central cup-shaped surface 24D that directs the tissue cut by the cutting edge 22D into the tissue chamber 12 (see FIG. 2). The cutting edge 22D may be at a radially outer edge 23D of the cutting element 4D when the cutting element is in the cutting position. In one embodiment the cup-shaped surface 24D may be a substantially smooth and continuous surface as described above in connection with the cutting element 4. As disclosed in another embodiment below (FIGS. 19 and 20), the cup-shaped surface 24D may be abrasive. In other embodiments, a through opening (not shown) may extend longitudinally through the cup-shaped surface 24D to direct removed tissue proximally through the cutting element 4D.

Figure 13:
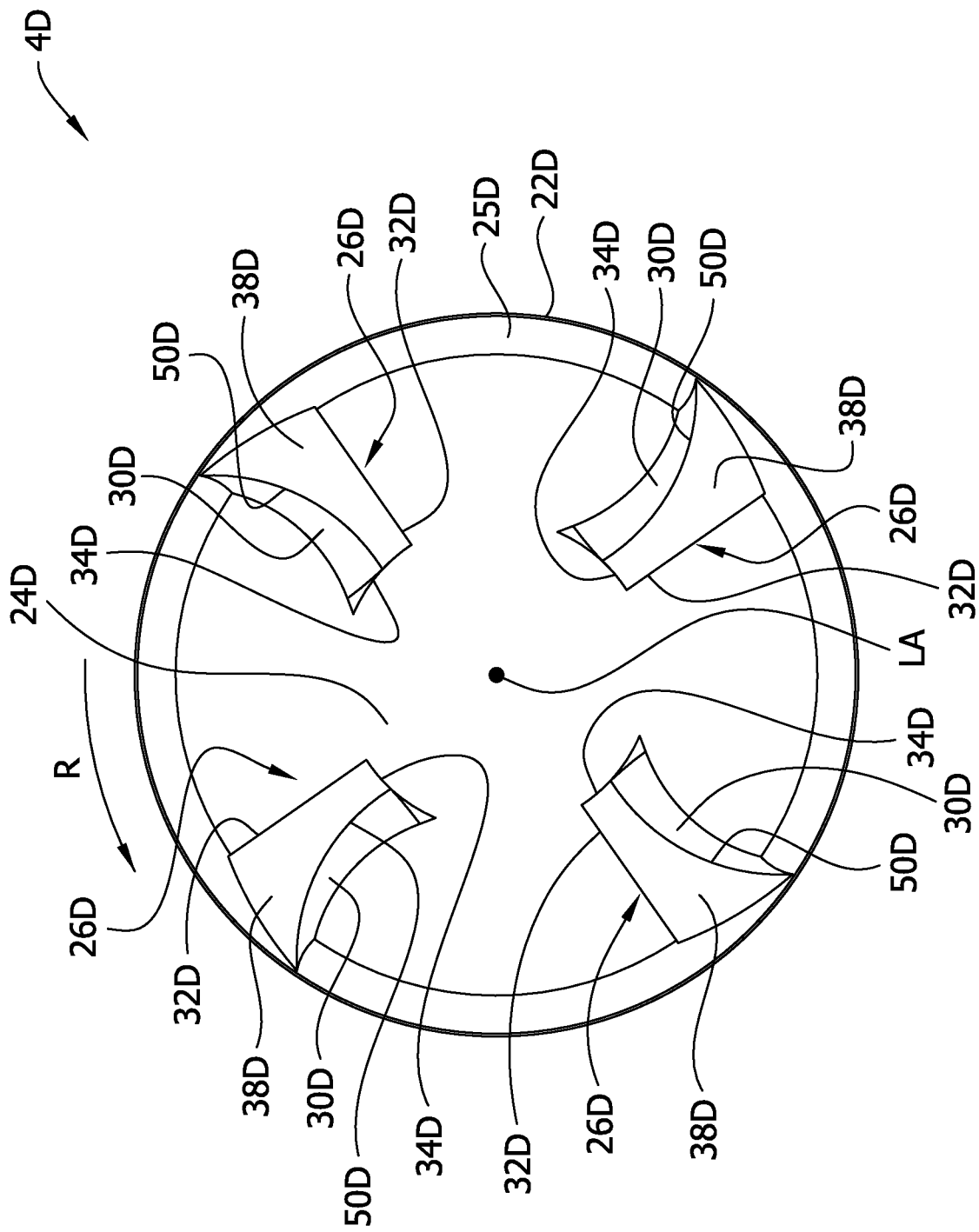
FIG. 13 is an end view of the cutting element of FIG. 12.

The raised elements 26D extend generally longitudinally outward from the cup-shaped surface 24B, within the internal cavity of the cutting element 4D. The embodiment illustrated in FIGS. 12-18 includes four raised elements 26D, but the cutting element 4D may include any number such as 1, 2, 3, 4, 6 or 8 raised elements. Each raised element 26D is a small wedge of material that rises relatively abruptly from the inner surface (e.g., the cup-shaped surface 24D) and which subtends an arc of about 1 to 30 degrees relative to axis LA, the four raised elements 26D subtending an arc of about 4 to 60 degrees altogether. Referring to FIG. 13, each raised element 26D has a leading radial wall (broadly, a first wall) 30D, a trailing radial wall (broadly, a second wall) 32D, a radially inner end wall 34D (broadly, a third wall), and a distal wall (broadly, a fourth wall) 38D. The leading radial wall 30D has a depth extending longitudinally relative to the cutter 4D between the distal wall 38D and the cup-shaped surface 24D, and a radial length RL (FIG. 15) extending generally inward from adjacent the cutting edge 22D of the cutting element 4D, as explained in more detail below. The leading radial wall 30D is curved along its depth (i.e., curved longitudinally with respect to the cutting element 4D) and is also curved along its radial length RL. A leading edge 50D of the cutting element 26D is defined at the intersection of the leading radial wall 30D and the distal wall 38D. The leading edge 50D is curved radially relative to the cutter 4D. In some embodiments the raised elements 26D may occupy a relative small part of the cup-shaped surface 24D and may be recessed from the cutting edge 22D in the manner described above in connection with the cutting element 4. In other embodiments at least 60%, 70%, 80% or 90% of the surface area of the cutting element is a smooth cup-shaped surface.

Figure 15:
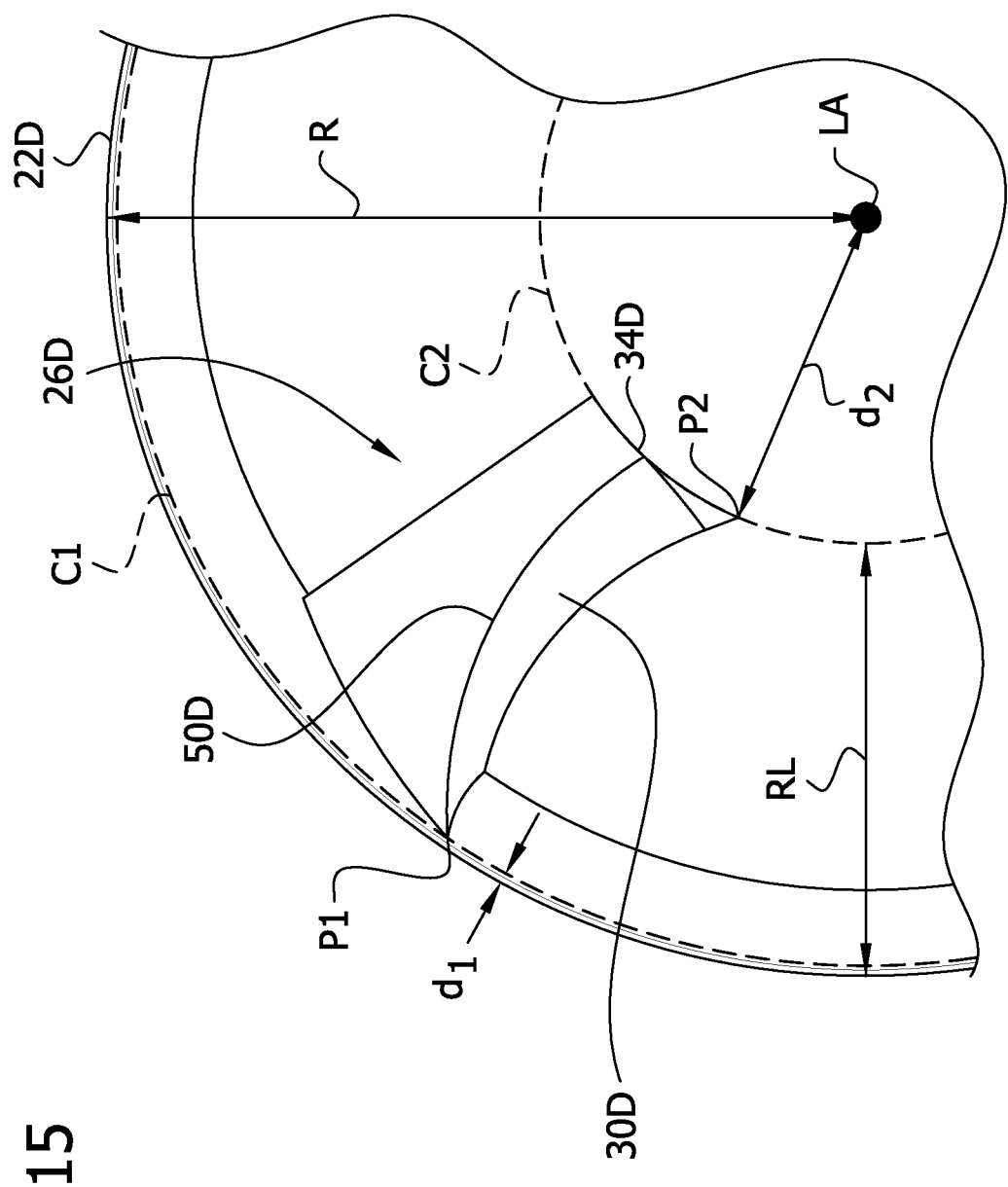
FIG. 15 is an enlarged, fragmentary view of FIG. 14.
Figure 16:
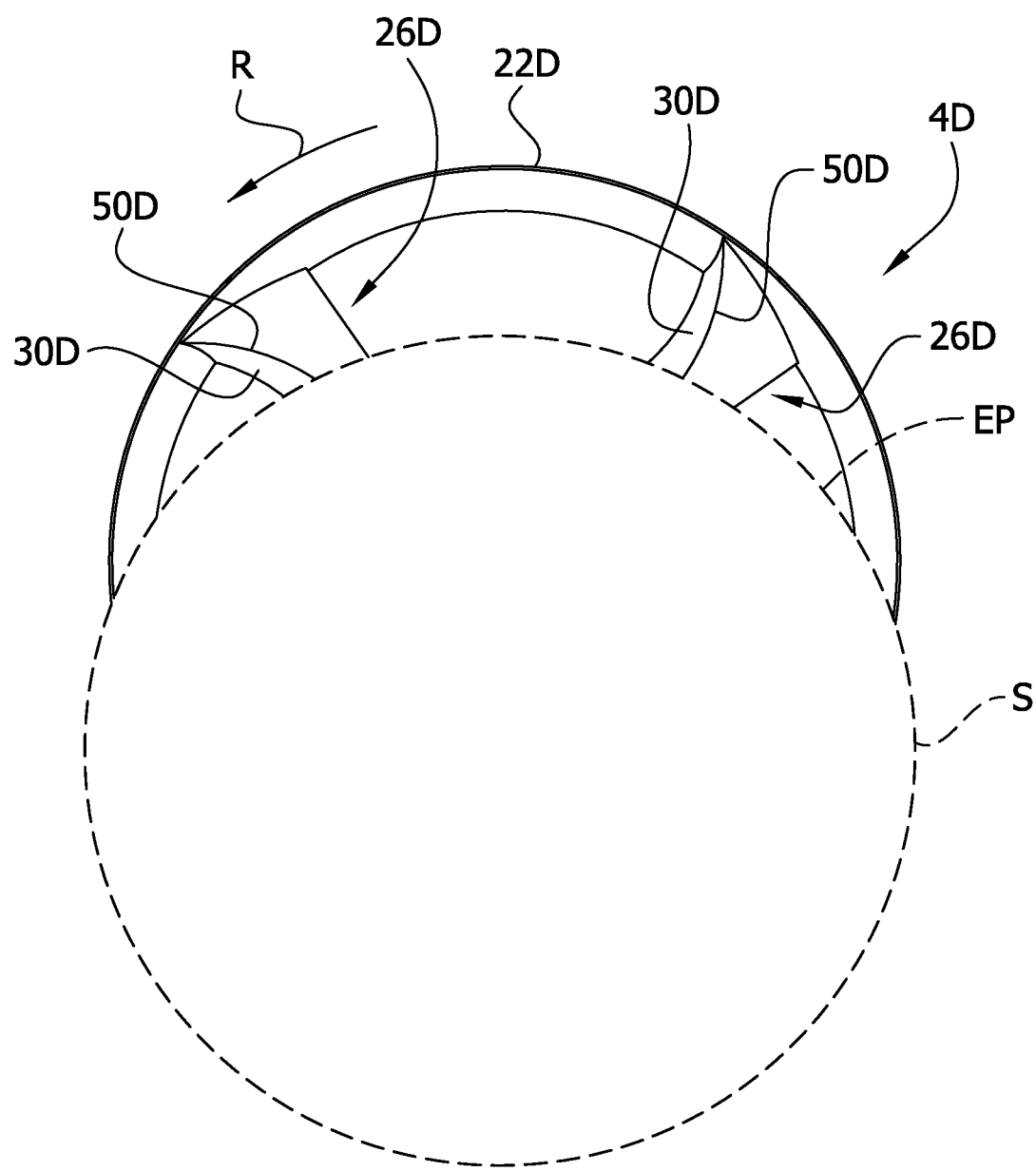
FIG. 16 is similar to FIG. 13, but including a schematic representation of the catheter body.

The distal wall 38D of the cutting element 4D forms an angle of less than 90 degrees with respect to the longitudinal axis LA. In some embodiments the wall 38D is angled such that edge 50D is more distal than the edge defined at the intersection of the distal wall 38D and the trailing wall 32D. The entire distal wall 38D may adjacent to, but recessed longitudinally from, the cutting edge 22D so that the distal wall is spaced a minimum longitudinal distance from about 0.0010 to about 0.0050 inch (0.0025 to 0.0127 cm), including about 0.0010, about 0.0020, about 0.0030, about 0.0040 or about 0.0050 inch (0.0025, 0.0051, 0.0076, 0.0101, or 0.0127 cm), from the cutting edge. The included angle between leading radial wall 30D and the distal wall 38D, in the vicinity of the leading edge 50D, may be greater than 90 degrees. The cutting element 4D is rotated in the direction R (FIG. 13) so that the leading edge 50D engages the tissue to be removed. As shown in FIG. 15, the leading edge 50D of the raised element 26D may be spaced a radial distance $d_1$ measuring from about 0.0010 to about 0.0020 inch (0.0025 to 0.0051 cm) from the cutting edge 22D. The raised elements 26D may all be formed in the same manner or may be different from one another. The raised elements 26D may also subtend different angles, be of different heights, have different radial lengths, or have a different spacing (including zero) from the cutting edge without departing from various aspects of the present invention.

Figure 14:
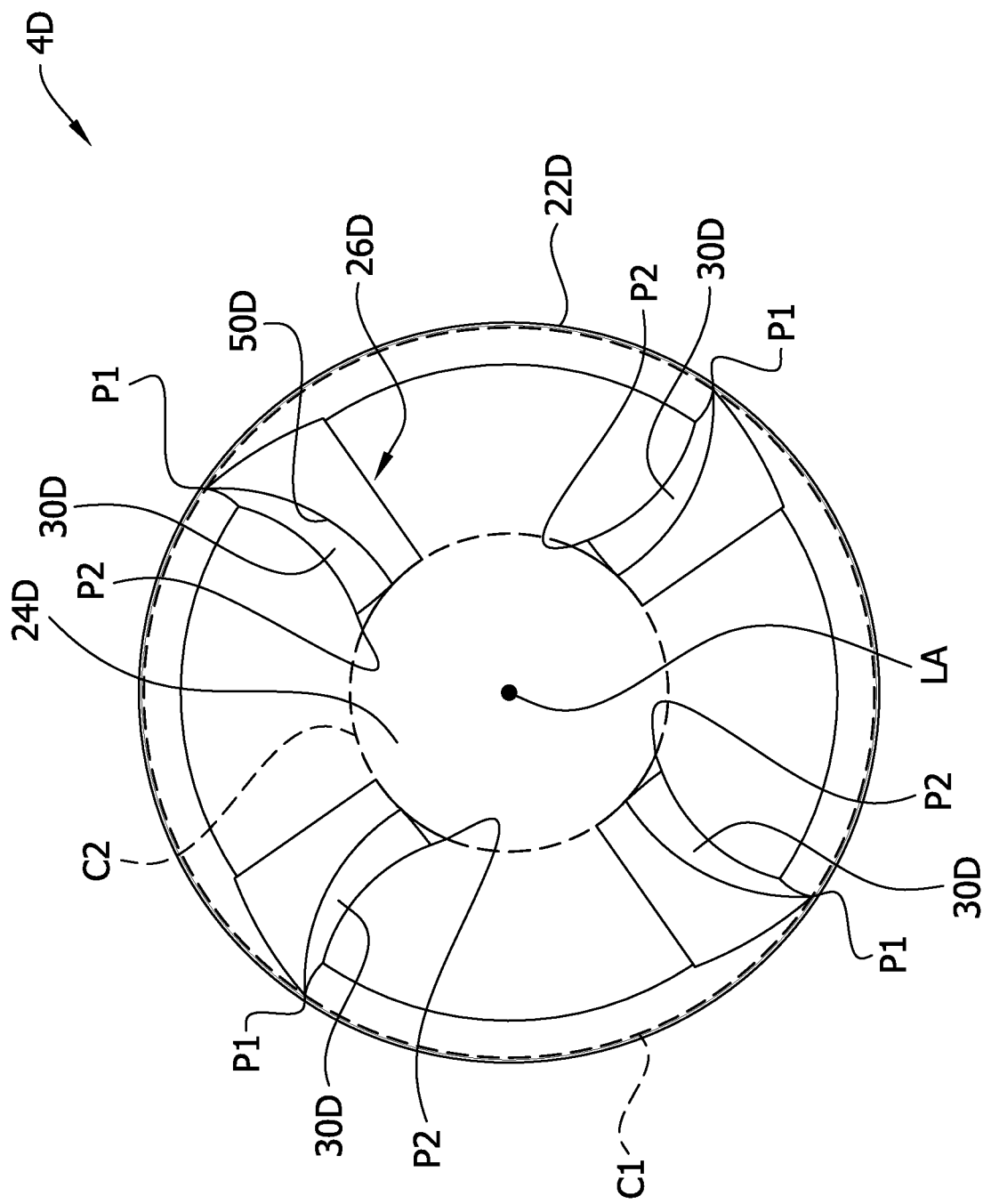
FIG. 14 is similar to FIG. 13, but enlarged and including imaginary circles for determining radial distances and radial lengths.

Referring to FIGS. 14 and 15, the radial length RL of the leading radial wall 30D of each raised element 26D is defined by the radial distance between the radially outermost portion P1 and the radially innermost portion P2 of the leading radial wall. In FIG. 15, the radial length RL of the radial wall 30D is measured using concentric, outer and inner imaginary circles C1, C2, respectively, each having a center that is coincident with the longitudinal axis LA. The radially outermost portion P1 of the leading radial wall 30D lies on the circumference of the outer imaginary circle C1, and the radially innermost portion P2 lies on the circumference of the inner imaginary circle C2. In the illustrated embodiment, each radially outermost portion P1 of the leading radial walls 30D lies on the circumference of the same outer imaginary circle C1, and each radially innermost portion P2 lies on the circumference of the same inner imaginary circle C2, though it is understood that the radially outermost and innermost portions, respectively, may not lie on the same imaginary circles without departing from the scope of the present invention. In the illustrated embodiment, the radially inner end wall 34D is arcuately shaped so that substantially the entire radially inner end wall lies on the circumference of the inner imaginary circle C2, although this may not be the case in other embodiments. The radial distance between the circumferences of the outer and inner imaginary circles C1, C2, respectively, determines the radial length RL of the leading radial wall 30D, as shown in FIG. 15. In one example, the radial length RL of the leading radial wall 30D may measure from about 0.0050 in to about 0.0200 in, or from about 0.0075 in to about 0.0175 in, or from about 0.0100 in to about 0.0150 in. In one example, the radial length RL of the leading radial wall may be at least about 33%, or at least about 40%, or at least about 50%, or at least about 60% or at least about 70% or at least about 80% of the radius R (FIG. 15) of the cutting edge 22D.

Referring still to FIG. 15, the radially innermost portion P2 of the leading radial wall 30D of each raised element 26D is spaced a radial distance $d_2$ from the longitudinal axis LA of the cutting element 4D. As set forth above, the radially innermost portion P2 of the leading radial wall 30D lies on the circumference of the inner imaginary circle C2. The radial distance between the longitudinal axis LA and the circumference of the inner imaginary circle C2 determines the radial distance $d_2$ between the longitudinal axis and the radially innermost portion P2 of the leading radial wall 30D. In one example, radial distance d between the longitudinal axis and the radially innermost portion P2 of the leading radial wall 30D may measure from about 0.0150 in to about 0.0300 in, or from about 0.0175 in to about 0.0275 in, or from about 0.0200 in to about 0.0250 in. In one example, the radial distance $d_2$ may be less than about 66%, or less than about 60%, or less than about 55%, or less than about 50%, or less than about 45%, or less than about 40%, or less than about 35% of the radius R of the annular cutting edge 22D, as shown in FIG. 15. In one example, the radial distance $d_2$ may be from about 15% to about 66%, or from about 20% to about 60%, or from about 25% to about 50%, or from about 30% to about 40% of the radius R of the annular cutting edge 22D.

Figure 17:
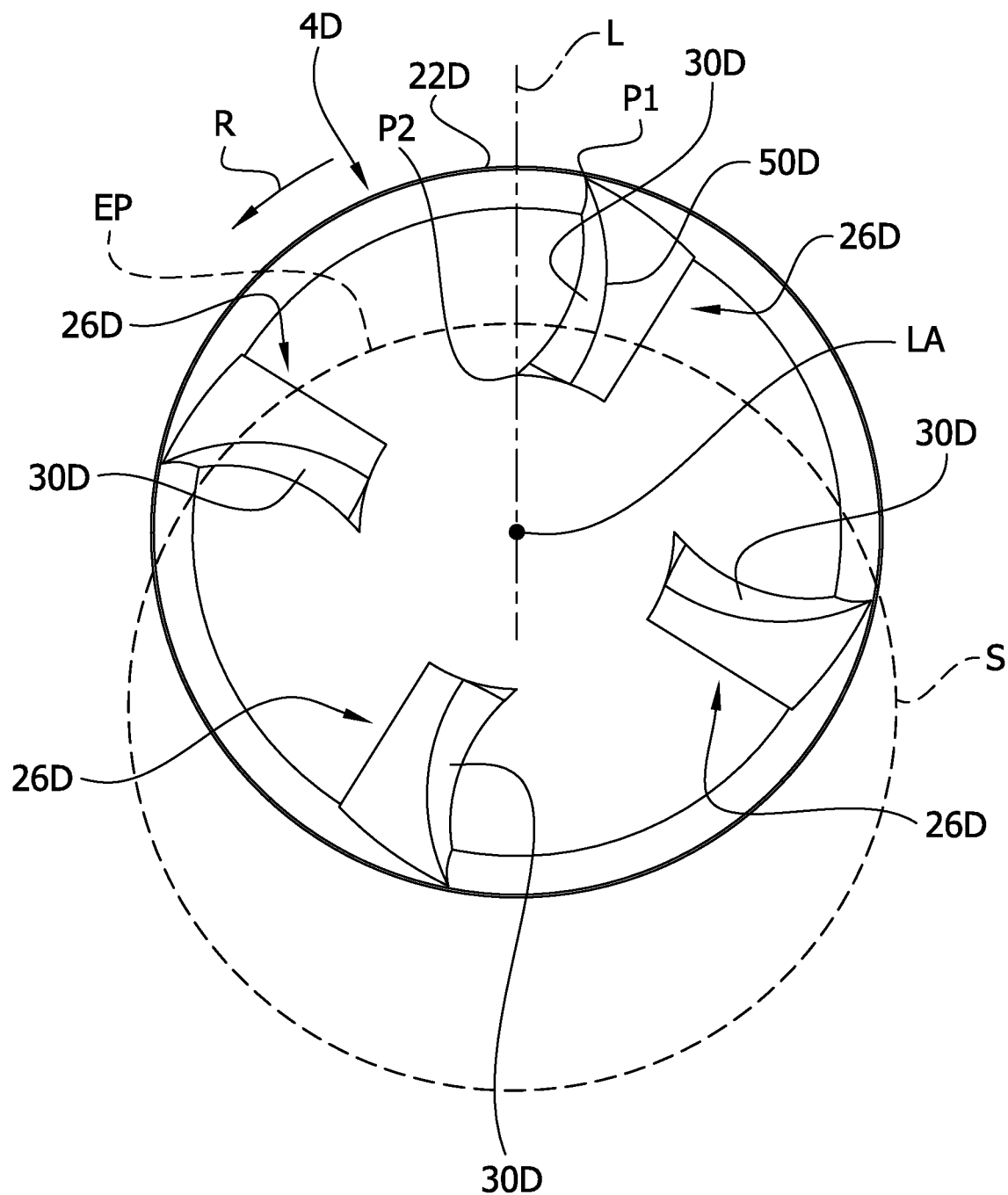
FIG. 17 is similar to FIG. 16, except the schematic representation of the catheter body is shown in phantom.

As disclosed above herein, in the deployed configuration the cutting element 4D extends through the window or opening 6 in the tip 18. In this embodiment, each raised element 26D is configured such that as the cutting element 4D is rotated 360 degrees, less than an entirety of the leading radial wall 30D is ever exposed through the opening 6. Stated another way, a radially outer portion of each raised element 26D is cyclically exposed through the opening 6 while a radial inner portion of the leading radial wall never passes through the opening (i.e., is never exposed). This feature is shown in FIG. 17, where the circle indicated by reference character S defines an outer surface of the tip 18 that is immediately adjacent the window 6 (see also, FIG. 16). As can be seen from FIG. 17, an imaginary line L is drawn to show the location where a radial portion of the cutting element 4D is at its maximum exposure outside the catheter body. However, as can be seen from this figure, a radial inner portion of the leading radial wall 30D of cutting element 26D at the imaginary line L does not cross the exposure plane EP and does not pass through the window 6.

Figure 18:
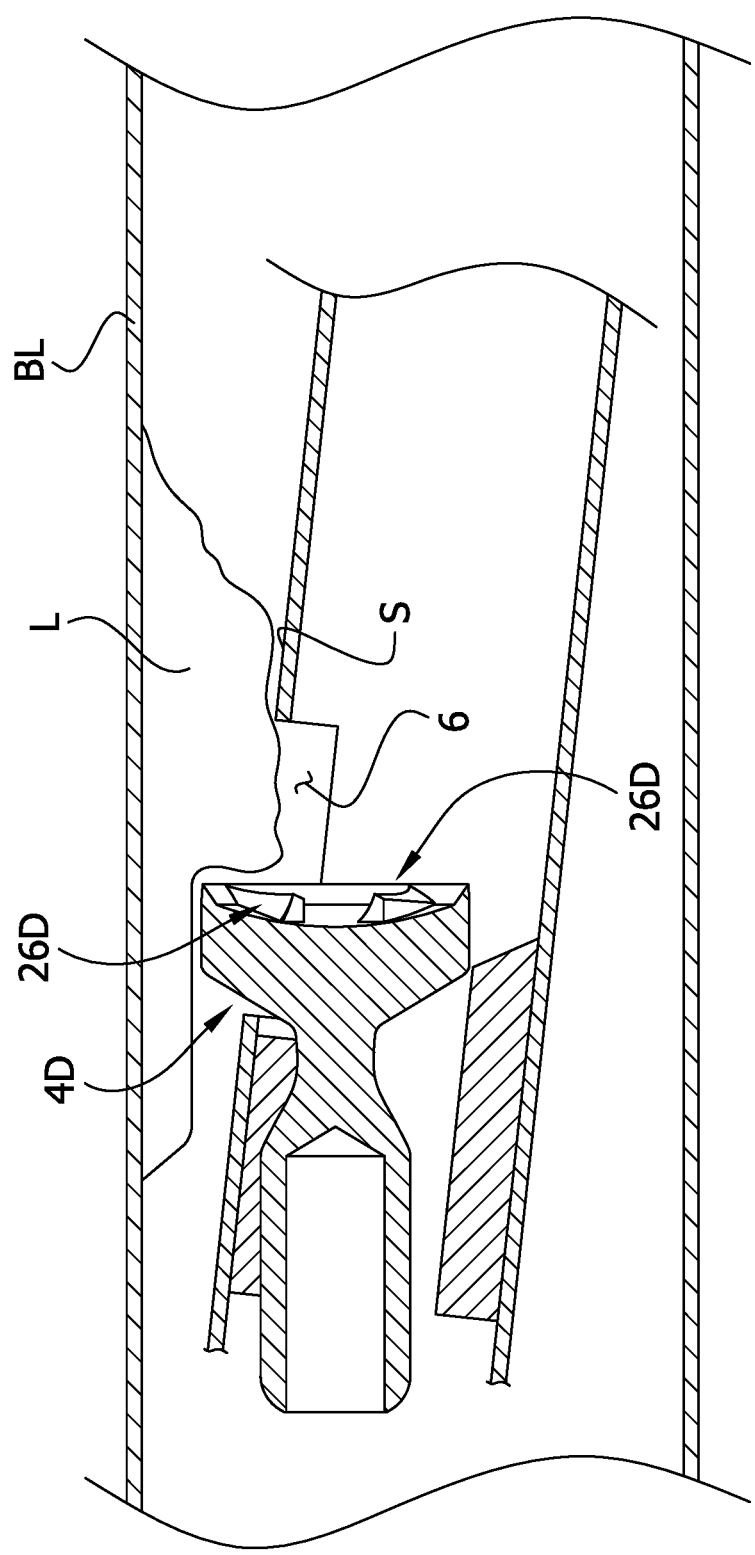
FIG. 18 is a fragmentary, longitudinal section of a catheter including the cutting element of FIG. 12 removing tissue from a body lumen.

The cutter 4D is rotated in the direction of arrow R and pushed distally to force cup-shaped surface 24D and raised elements 26D into contact with material such as atheroma or plaque. Raised elements 26D will tend to concentrate cutting force along edge 50D because of the negative rake angle of the leading radial wall 30D. Cutter 4D will tend to scrape away material such as atheroma or plaque rather than cut into this material due to the obtuse included angle between wall 30D and distal wall 38D, in the vicinity of edge 50D. Material contacted by raised elements 26D will tend to be directed toward axis LA by surface 30D which curves from a more circumferential extent near edge 22D to a more radial extent near edge 34D. Moreover, it is believed that configuring the raised element(s) 26D so that only a portion of the leading radial wall 30D intermittently passes through the window 6 (i.e., only a portion and not the entirety of the leading radial wall is exposed) and is intermittently exposed (as explained above), facilitates cutting and/or breaking of hardened tissue (e.g., calcified tissue) by ensuring that the raised elements 26D engage tissue that may enter the window 6, as shown in FIG. 18. The leading radial wall 30D also more reliably guides or directs removed material toward the axis LA.

The cutting element 4D may be formed in a suitable manner such as integrally as a single, one-piece construction. For example, the cutting element 4D may be comprised of steel, tungsten carbide, tungsten carbide cobalt, tungsten carbide molybdenum, silicon carbide, silicon nitride, ceramic, amorphous metals or other materials and may be manufactured by methods including turning, grinding, sintering, electro-discharge machining (EDM), laser cutting, heat treating, precipitation hardening, casting or other methods.

Figure 19:
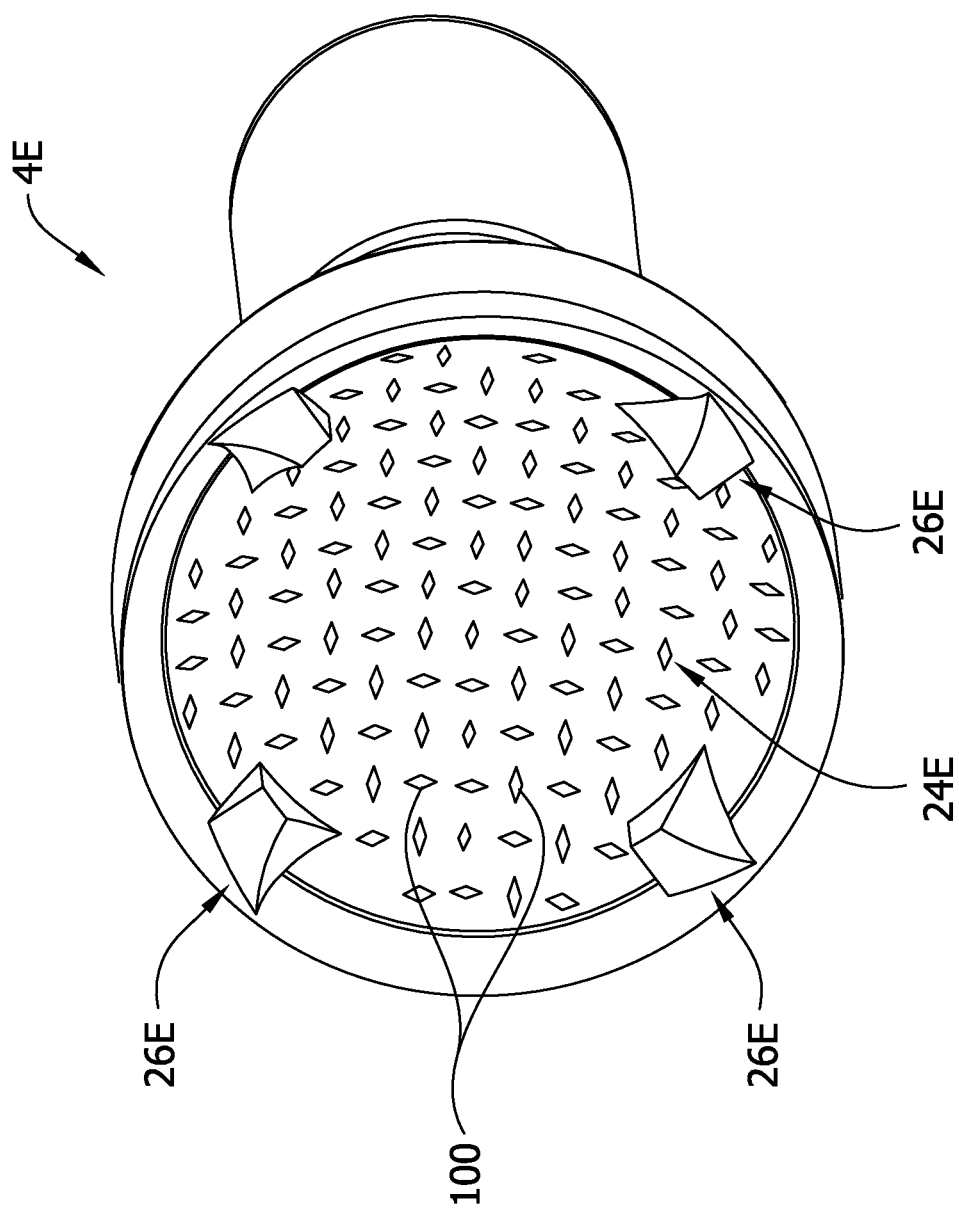
FIG. 19 is a perspective of another embodiment of a cutting element.
Figure 20:
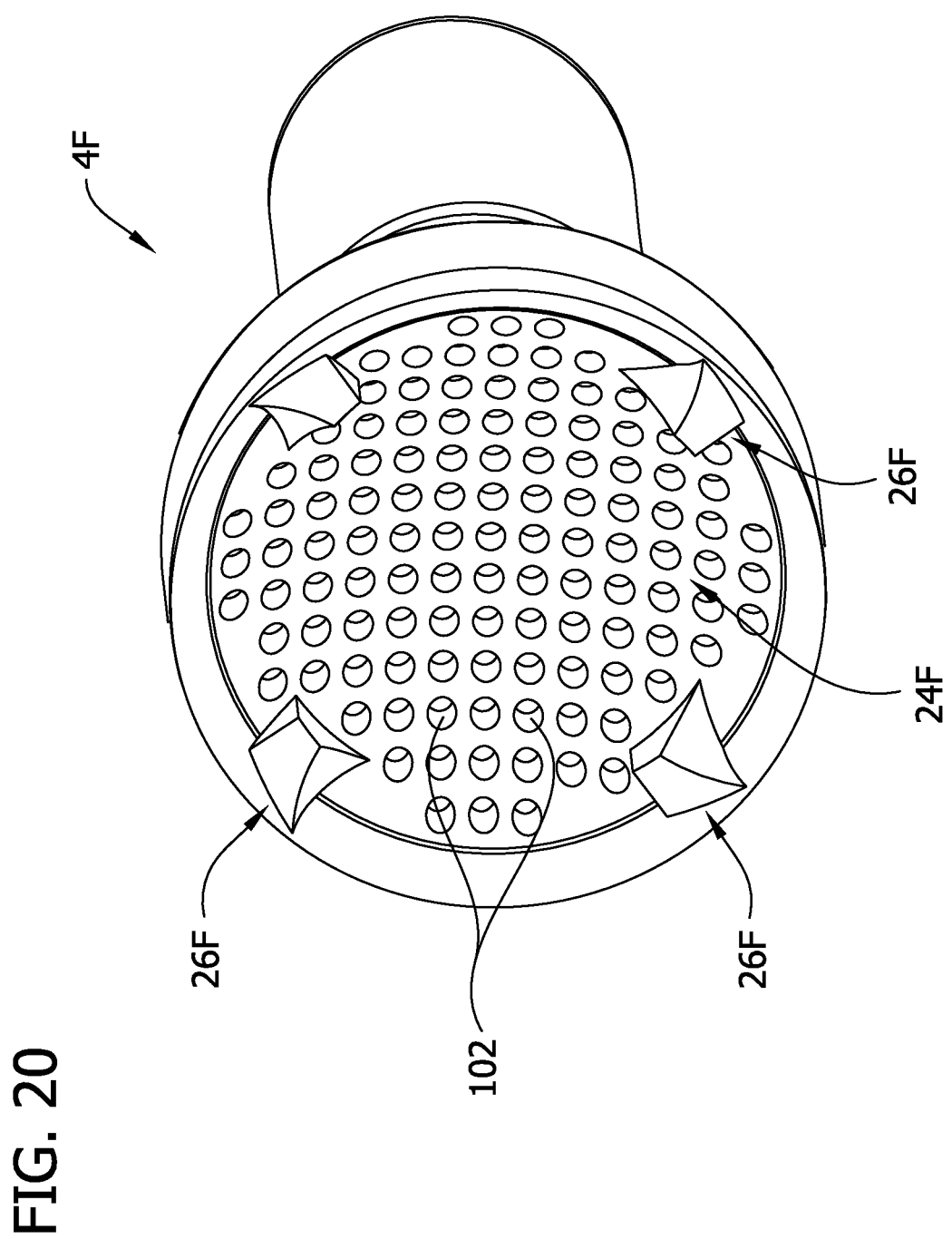
FIG. 20 is a perspective of another embodiment of a cutting element.
Figure 21:
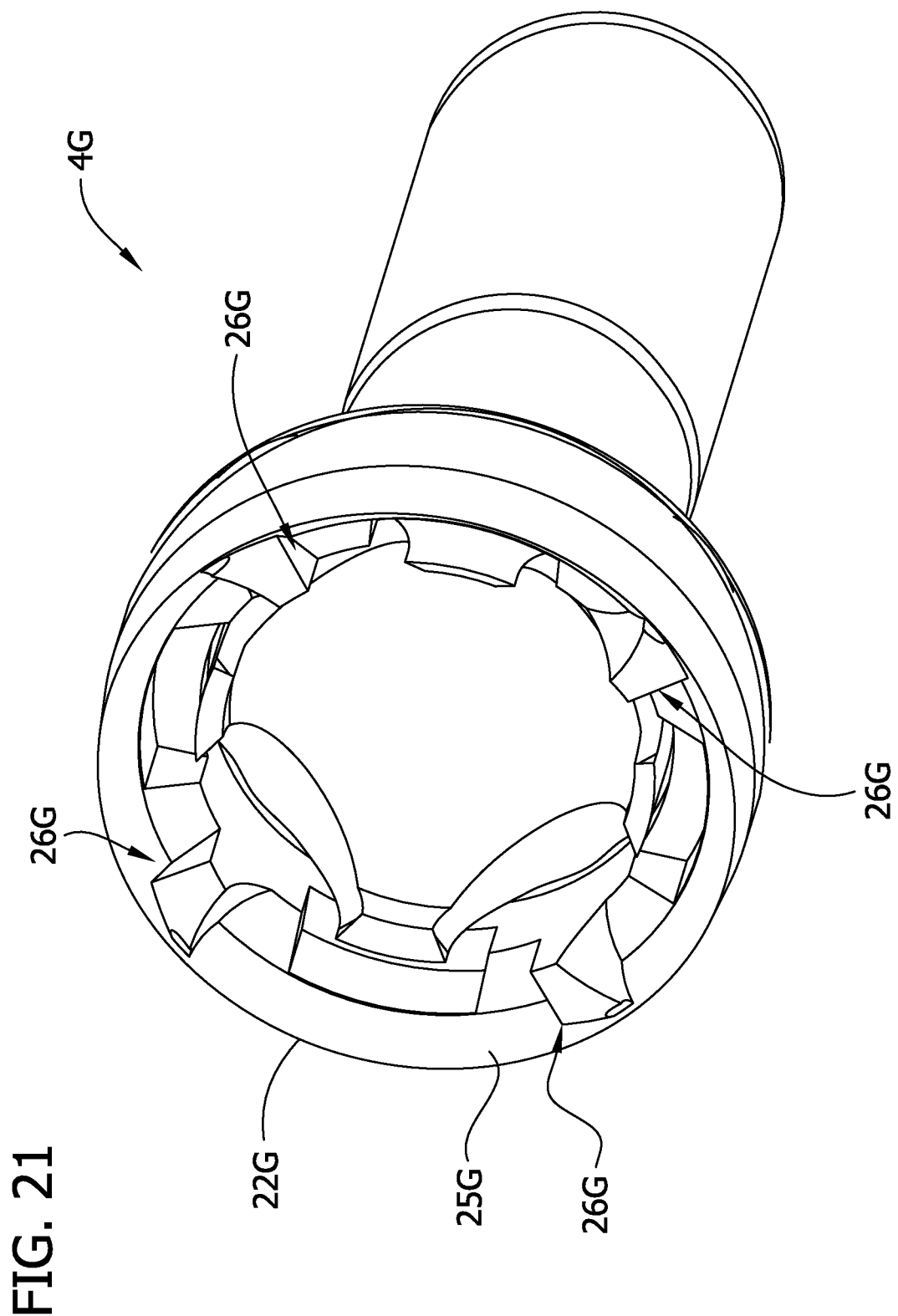
FIG. 21 is a perspective of another embodiment of a cutting element.
Figure 22:
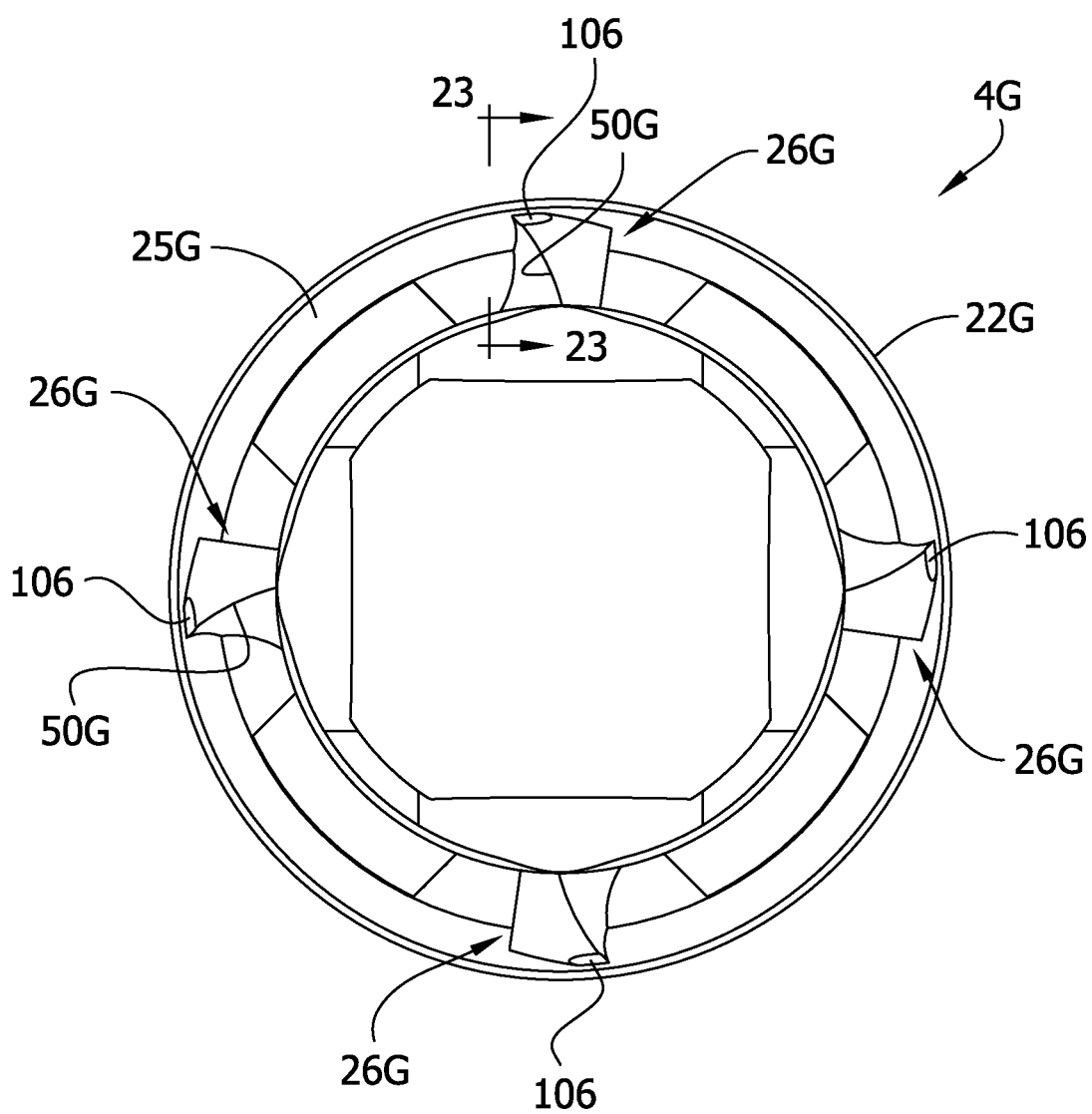
FIG. 22 is an end view of the cutting element of FIG. 21.
Figure 23:
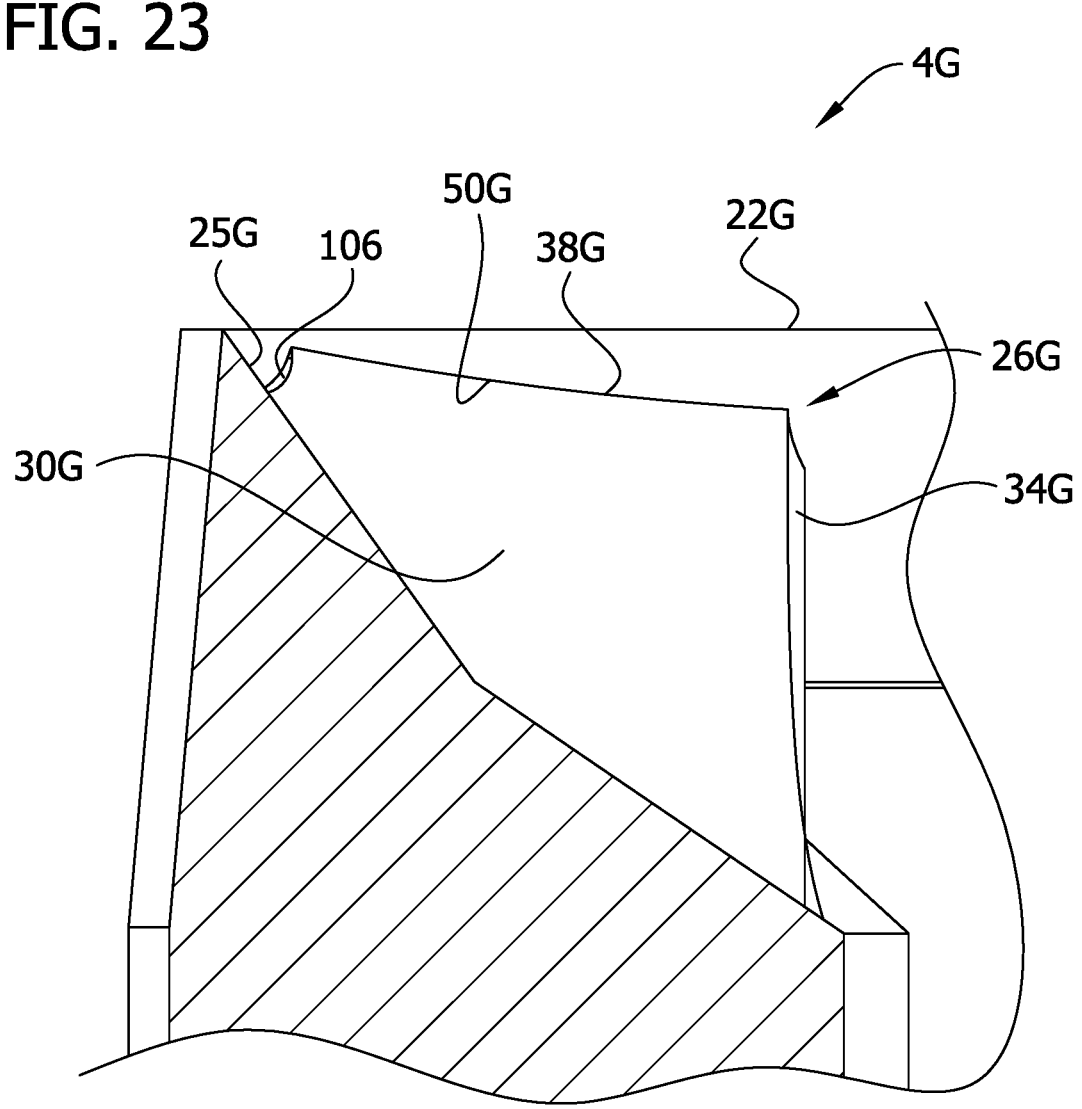
FIG. 23 is an enlarged, fragmentary section of the cutting element taken in the plane containing the line 23-23 in FIG. 22.

Referring to FIGS. 19 and 20, cutting elements 4E and 4F are shown (respectively). Cutting element 4E and 4F include raised elements 26E, 26F, that may be identical to the raised elements 26A-26D of any of the previously disclosed cutting element 4A-4D disclosed above or have a different configuration. Accordingly, the teachings of the raised elements 26A-26D set forth above are incorporated in this embodiment. As opposed to the previously disclosed cutting elements, the cutting elements 4E and 4F each has an abrasive cup-shaped surface 24E, 24F. In one embodiment, other than the abrasive cup-shaped surface 24E, 24F, the cutting elements 4E and 4F are identical to the cutting element 4D, including the raised elements 26E being identical to the raised elements 26D. Accordingly, in this embodiment each of the cutting elements 4E and 4F includes the cutting element 4D and the respective one of the abrasive cup-shaped surfaces 24E, 24F. Referring to FIG. 19, cutting element 4E includes the embossed area of the cup-shaped surface 24E, including raised, diamond-shaped abrading members 100. Referring to FIG. 20, cutting element 4F includes a dimpled area of the cup shape surface 24F including depressed portions 102. In each embodiment, the abrasive cup-shaped surface 24E, 24F abrades hardened tissue (e.g., calcified tissue), and in particular, the abrasive cup-shaped surface abrades hardened tissue that is not engaged by the raised elements 26E. Thus, it is believed that the cutting elements 4E and 4F may more effectively remove hardened tissue compared to the cutting element 4, which is free from an abrading surface.

The cutting elements 4E and 4F each may be formed integrally as a single, one-piece construction, or may be formed as a multiple-piece construction. As an example, each cutting element 4E and 4F may be comprised of steel, tungsten carbide, tungsten carbide cobalt, tungsten carbide molybdenum, silicon carbide, silicon nitride, ceramic, amorphous metals or other materials and may be manufactured by methods including turning, grinding, sintering, electro-discharge machining (EDM), laser cutting, heat treating, precipitation hardening, casting or other methods.

Referring to FIGS. 21-25, another embodiment of a cutting element is indicated generally at 4G. The cutting element 4G is similar to the cutting element 4B, and therefore, like components are indicated by similar reference numerals, and the teachings set forth with respect to the cutting element 4B apply equally to this embodiment. Briefly, each raised element 26G of the cutting element 4G has a leading wall 30G, a radial inner end wall 34G, a distal wall 38G, and a leading edge 50G. For purposes of this disclosure, the main difference between the present cutting element 4G and the prior cutting element 4B is that the radial distance between the leading edge 50G of each raised element 26G and the cutting edge 22G of the present cutting element 4G is greater than the radial distance between the leading edge 50B of each raised element 26B and the cutting edge 22B of the cutting element 4B. It is understood that the teachings set forth herein for the cutting element 4G apply equally to the other cutting elements 4A-4F.

Figure 24:
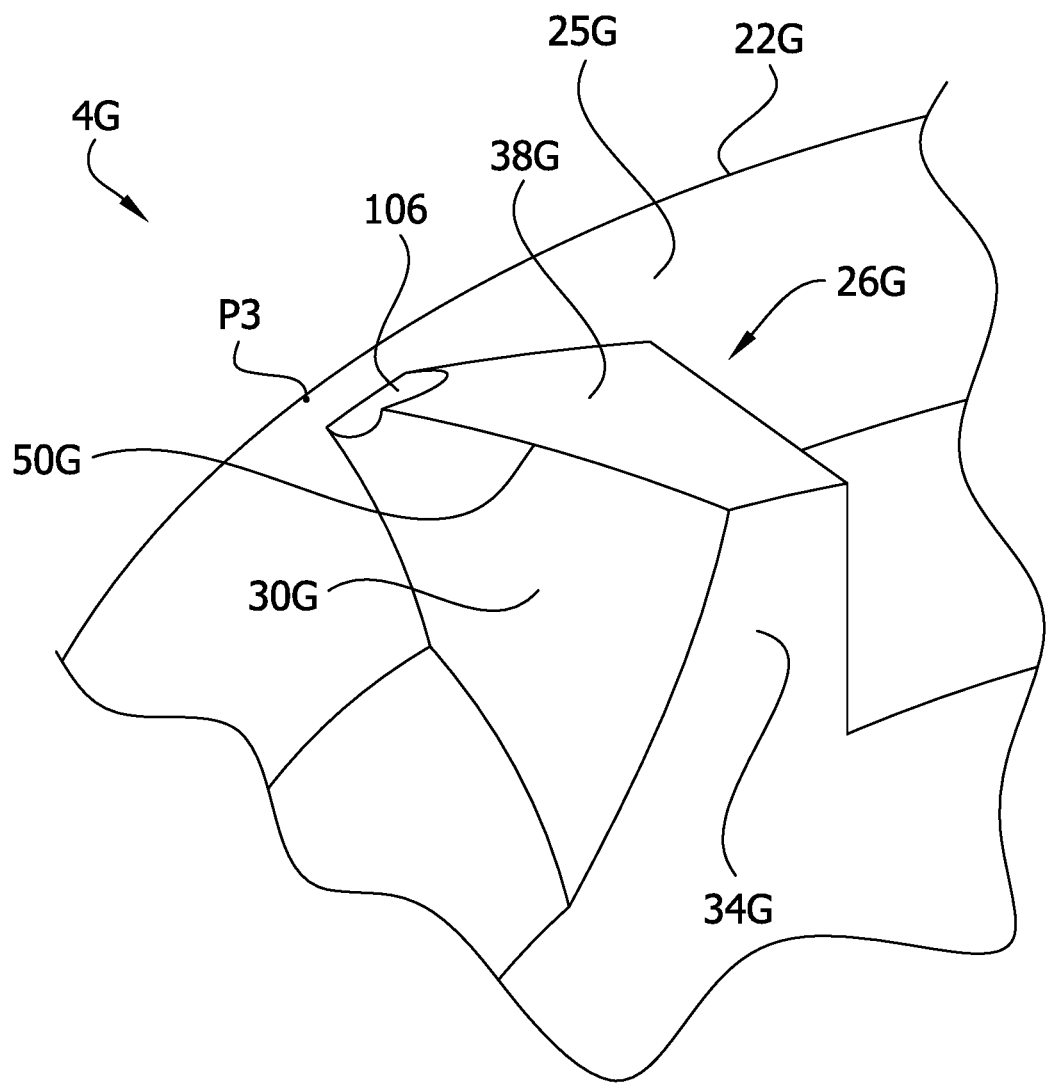
FIG. 24 is an enlarged view of a raised element of the cutting element of FIG. 21.
Figure 25:
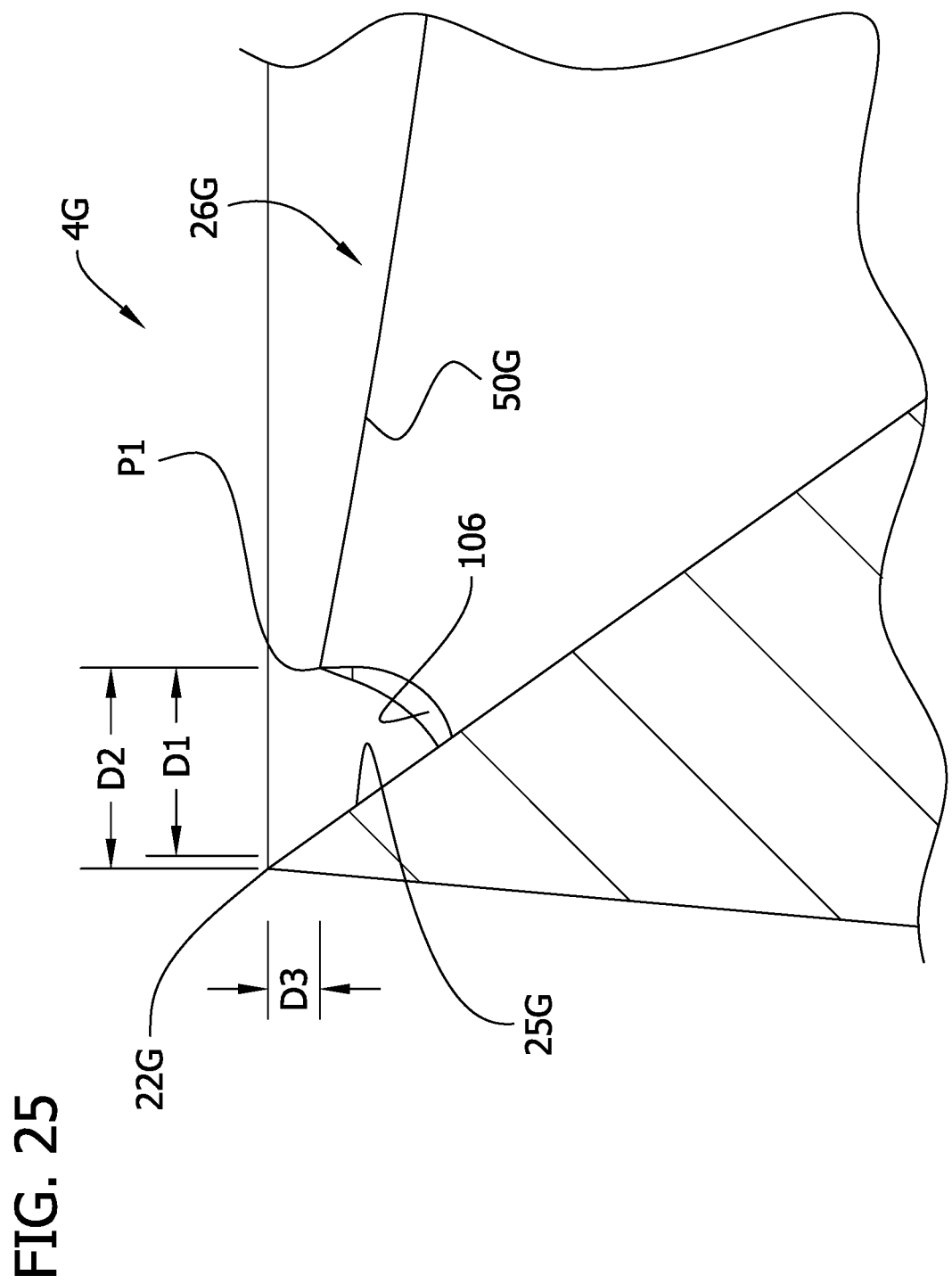
FIG. 25 is a further enlarged, fragmentary view of FIG. 23.

In the illustrated example, the present cutting element 4G includes an undercut (e.g., groove, recess, notch or cutout) 106 in each of the raised elements 26G adjacent the cutting edge 22G. The undercut 106 extends through the leading wall 30G, the leading edge 50G, and the distal wall 38G of each raised element 26G. The undercut 106 extends generally radially into the raised element 26G at the radially outermost portion of the raised element. As best seen in FIG. 24, the undercut 106 has a circumferential extent almost perpendicular to the wall 30G. The depth of the undercut 106 shallows slightly circumferentially away from the leading edge 50G. In contrast, the undercut 41C of FIGS. 11 and 11A extends circumferentially into the raised element 26C and has a generally radial extent along the wall 30C. As shown best in FIG. 25, because of the undercut 106, the radially outermost portion P1 of the leading edge 50G of the cutting element 4G is radially spaced from the chamfered circumferential inner surface 25G (broadly, the inner surface) of the cutting element a radial distance D1 (FIG. 25). In one example, the radial distance D1 may measure from greater than 0.0000 in to about 0.0100 in, or from greater than 0.0000 to about 0.0050 in, or from about 0.0005 in to about 0.0015 in. The radially outermost portion P1 of the leading edge 50G is radially spaced from the cutting edge 22G of the cutting element 4G a distance D2, which is greater than the radial distance between the leading edge 50B and the cutting edge 22B of the cutting element 4B. In one example, the distance D2 may measure from greater than 0.0000 in to about 0.0100 in, or from greater than 0.0000 to about 0.0050 in, or from about 0.0005 in to about 0.0020 in. Moreover, the leading edge 50G of the cutting element 4G may be spaced a minimum longitudinal distance D3 from the cutting edge 22G. In one example, the distance D3 may measure from about 0.0000 to about 0.0020 in. In one example, the leading edge 50G is similar to the leading edge 50B, except for the undercut 106, and therefore, an imaginary extrapolated line extending from the leading edge 50G intersects the chamfered inner surface 25G of the cutting element 4G at portion P3 (FIG. 24), which may be substantially the same location as the radially outermost portion P1 of the raised element 26B (see, e.g., FIG. 14).

It is believed that by spacing the leading edges 50G of the raised elements 26G from the chamfered inner circumferential portion 25G of the cutting element 4G, while maintaining a suitable minimum longitudinal distance between the cutting edge 22G and the leading edges of the raised elements, the raised elements 26G have better engagement with tissue than the cutting element 4B, without sacrificing cutting efficiency of the cutting element.

The cutting elements 4G may be formed integrally as a single, one-piece construction, or may be formed as a multiple-piece construction. As an example, the cutting element 4G may be comprised of steel, tungsten carbide, tungsten carbide cobalt, tungsten carbide molybdenum, silicon carbide, silicon nitride, ceramic, amorphous metals or other materials and may be manufactured by methods including turning, grinding, sintering, electro-discharge machining (EDM), laser cutting, heat treating, precipitation hardening, casting or other methods.

Use of the catheter 2 is now described in connection with the cutting element 4 but is equally applicable to use of the catheter 2 with either the cutting element 4A, the cutting element 4B, or the cutting element 4C. The catheter 2 is introduced into the patient in a conventional manner using a guidewire (not shown) or the like. The catheter 2 is advanced with the cutting element in the stored position of FIG. 2 until the catheter is positioned proximal to the location where material is to be removed. The cutting element 4 is then moved proximally so that the ramp 16 and cam surface 14 engage to move the cutting element 4 to the cutting position of FIG. 3 and to deflect the tip of the catheter 2 to move the cutting element 4 toward the tissue to be cut. The cutting element 4 is rotated about longitudinal axis LA and catheter 2 is then moved distally through the vessel so that the cutting element 4 cuts tissue. The tissue, which has been cut, is directed into the tissue chamber 12 by the cup-shaped surface 24, one or more raised elements 26, by curved surface 30B (of cutting element 4B), or by any combination of a cup-shaped surface, raised element, or curved surface. The location for collection of cut tissue may be other than described within the scope of the present invention.

More specifically, when using cutting element 4B and rotating the cutting element in the direction of arrow R (FIG. 9) cutting edge 22B slices softer material and cup-shaped surface directs the cut material into tissue chamber 12; the relief angle assures that distally directed force on the catheter is concentrated at raised element edge 50B rather than distributed over wall 38B; raised elements 26B will tend to scrape away or pulverize harder material such as calcium due to the obtuse included angle between leading radial wall 30B and distal wall 38B in the vicinity of edge 50B; curved surface 30B directs material particles towards cutter axis LA; and curved surface 30B when rotating creates a fluid vortex that tends to direct material particles towards cutter axis LA and distally into tissue chamber 12.

More specifically, when using an undercut such as that shown for cutting element 4C and rotating the cutting element in the direction of arrow T (FIG. 11) undercut 41C directs material away from cutting edge 22A, along cup-shaped surface towards axis LA, and radially towards axis LA of the cutting element.

More specifically, when using the cutting element 4D with raised elements 26D having leading radial walls 30D as set forth above, the raised elements facilitate cutting and/or breaking of hardened tissue (e.g., calcified tissue) by ensuring that the raised elements 26D engage tissue that may enter the window 6, as shown in FIG. 18.

When using the cutting elements 4E or 4F, the abrasive cup-shaped surface 24E, 24F abrades hardened tissue (e.g., calcified tissue), and in particular, the abrasive cup-shaped surface abrades hardened tissue that is not engaged by the raised elements 26E.

When using the cutting element 4G, the raised elements 26G have improved engagement with tissue, as compared to the cutting element 4B, without sacrificing cutting efficiency of the cutting element.

Having described the invention in detail, it will be apparent that modifications and variations are possible without departing from the scope of the invention defined in the appended claims.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A tissue-removing catheter comprising:
   an elongate catheter body having opposite distal and proximal portions and being sized and shaped for introduction into a body lumen of a subject, the catheter body having a window at the distal portion thereof;
   a drive shaft extending longitudinally within the catheter body, wherein the drive shaft is rotatable relative to the catheter body about a longitudinal axis of the drive shaft;
   a cutting element at the distal portion of the elongate catheter body adjacent the window, the cutting element having opposite proximal and distal ends and a longitudinal axis extending therebetween, the cutting element being operatively connected to the drive shaft for rotation about the longitudinal axis of the cutting element, the cutting element being extendable through the window in an extended position, the cutting element including
      an annular cutting edge at the distal end of the cutting element surrounding the longitudinal axis of the cutting element, the annular cutting edge having a radius as taken from the longitudinal axis of the cutting element,
      an inner surface extending proximally from the cutting edge and defining an internal cavity,
      at least one raised element in the internal cavity having leading radial wall extending generally radially inward toward the longitudinal axis of the cutting element,
   wherein the leading radial wall has a radially outermost portion relative to the longitudinal axis of the cutting element, and a radially innermost portion relative to the longitudinal axis of the cutting element,
   wherein when the cutting element is in its extended position, the radially outermost portion of the leading radial wall is configured to pass through the window as the cutting element is rotated 360 degrees about its longitudinal axis,
   wherein when the cutting element is in its extended position, the radially innermost portion of the leading radial wall is configured to remain in the elongate catheter body and not pass through the window as the cutting element is rotated 360 degrees about its longitudinal axis.

2. The tissue-removing catheter set forth in claim 1, wherein the leading radial wall has a radial length extending between the radially outermost and innermost portions, wherein the radially innermost portion of the leading radial wall is spaced a radial distance from the longitudinal axis that is less than about 66% of the radius of the annular cutting edge.

3. The tissue-removing catheter set forth in claim 2, wherein said radial distance is from about 15% to less than 66% of the radius of the annular cutting edge.

4. The tissue-removing catheter set forth in claim 3, wherein said radial distance is from about 20% to about 60% of the radius of the annular cutting edge.

5. The tissue-removing catheter set forth in claim 4, wherein said radial distance is from about 30% to about 40% of the radius of the annular cutting edge.

6. The tissue-removing catheter set forth in claim 2, wherein the radial length of the leading radial wall is at least about 33% of the radius of the annular cutting edge.

7. The tissue-removing catheter set forth in claim 2, wherein the radially outermost portion is spaced apart radially from the inner surface of the cutting element.

8. The tissue-removing catheter set forth in claim 1, wherein the at least one raised element comprises a plurality of raised elements.

9. The tissue-removing catheter set forth in claim 1, wherein at least a central portion of the inner surface is generally cup-shaped, the tissue-removing catheter further comprising a plurality of abrading members formed on at least the central portion of the inner surface, wherein the abrading members are adapted to abrade hardened tissue as the cutting element is rotating about its longitudinal axis.

* * * * *